United States Patent
Arcot Desai et al.

(10) Patent No.: US 11,439,826 B2
(45) Date of Patent: Sep. 13, 2022

(54) SYSTEMS AND METHODS FOR CLINICAL DECISION MAKING FOR A PATIENT RECEIVING A NEUROMODULATION THERAPY BASED ON DEEP LEARNING

(71) Applicant: NeuroPace, Inc., Mountain View, CA (US)

(72) Inventors: Sharanya Arcot Desai, Sunnyvale, CA (US); Thomas K. Tcheng, Pleasant Hill, CA (US)

(73) Assignee: NeuroPace, Inc., Mountain View, CA (US)

( * ) Notice: Subject to any disclaimer, the term of this patent is extended or adjusted under 35 U.S.C. 154(b) by 47 days.

(21) Appl. No.: 16/906,914

(22) Filed: Jun. 19, 2020

(65) Prior Publication Data
US 2020/0316383 A1    Oct. 8, 2020

Related U.S. Application Data

(63) Continuation of application No. 15/849,492, filed on Dec. 20, 2017, now Pat. No. 10,729,907.
(Continued)

(51) Int. Cl.
*A61N 1/36* (2006.01)
*A61N 1/05* (2006.01)
(Continued)

(52) U.S. Cl.
CPC ....... *A61N 1/36139* (2013.01); *A61N 1/0534* (2013.01); *A61N 1/37247* (2013.01);
(Continued)

(58) Field of Classification Search
CPC . A61B 5/4836; A61B 5/0476; A61B 5/04012; A61B 5/7282; A61B 5/0006;
(Continued)

(56) References Cited

U.S. PATENT DOCUMENTS 6,016,449 A    1/2000  Fischell et al.
6,480,743 B1   11/2002 Kirkpatrick et al.
(Continued)

FOREIGN PATENT DOCUMENTS

WO    2016154298 A1    9/2016

OTHER PUBLICATIONS

Ali Hossam Shoeb et al. "Application of Machine Learning to Epileptic Seizure Detection", Appearing in the Proceedings of the 27th International Conference on Machine Learning, Haifa, Israel 2010, Copyright 2010.
(Continued)

*Primary Examiner* — Deborah L Malamud
(74) *Attorney, Agent, or Firm* — Loza & Loza, LLP; David S. Sarisky

(57) ABSTRACT

Information relevant to making clinical decisions for a patient is identified based on electrical activity records of the patient's brain and electrical activity records of other patients' brains. A deep learning algorithm is applied to an electrical activity record of the patient, i.e., an input record, and to a set of electrical activity records of other patients, i.e., a set of search records, to obtain an input feature vector of the patient and a set of search feature vectors, each including features extracted by the deep learning algorithm. A similarities algorithm is applied to the input feature vector and the set of search feature vectors to identify a subset of search records most like the input record. Clinical information associated with one or more search records in the identified subset of search records is extracted from a database and used to make decisions regarding the patient's neuromodulation therapies.

21 Claims, 13 Drawing Sheets

Related U.S. Application Data

(60) Provisional application No. 62/575,351, filed on Oct. 20, 2017.

(51) Int. Cl.
*A61N 1/372* (2006.01)
*G16H 20/70* (2018.01)

(52) U.S. Cl.
CPC ...... *A61N 1/36064* (2013.01); *A61N 1/36171* (2013.01); *A61N 1/36175* (2013.01); *A61N 1/36178* (2013.01); *G16H 20/70* (2018.01)

(58) Field of Classification Search
CPC ....... A61B 5/6868; A61B 5/7267; A61B 5/00; A61B 5/0031; A61B 5/4064; A61B 5/748; A61B 5/7264; A61B 5/7275; A61B 5/0022; A61B 5/04; A61B 5/04001; A61B 5/04004; A61B 5/4848; A61B 5/486; A61B 5/0484; A61B 5/0482; A61B 5/7246; A61N 1/3605; A61N 1/36146; A61N 1/05; A61N 1/36; A61N 1/36034; A61N 1/00; A61N 1/08; A61N 1/36031; A61N 1/37514; G16H 50/20; G16H 50/50; G16H 50/30; G16H 50/70; G16H 10/60; G06F 3/015; G06K 9/00536; G06N 20/00

See application file for complete search history.

(56) References Cited

U.S. PATENT DOCUMENTS

| | | | |
|---|---|---|---|
| 6,810,285 B2 | 10/2004 | Pless et al. |
| 7,209,787 B2 | 4/2007 | Dilorenzo |
| 7,231,254 B2 | 6/2007 | Dilorenzo |
| 7,242,984 B2 | 7/2007 | Dilorenzo |
| 7,277,758 B2 | 10/2007 | Dilorenzo |
| 7,280,867 B2 | 10/2007 | Frei et al. |
| 7,324,851 B1 | 1/2008 | Dilorenzo |
| 7,403,820 B2 | 7/2008 | Dilorenzo |
| 7,529,582 B1 | 5/2009 | Dilorenzo |
| 7,542,803 B2 | 6/2009 | Heruth et al. |
| 7,599,736 B2 | 10/2009 | Dilorenzo |
| 7,623,928 B2 | 11/2009 | Dilorenzo |
| 7,676,273 B2 | 3/2010 | Goetz et al. |
| 7,747,325 B2 | 6/2010 | Dilorenzo |
| 7,822,481 B2 | 10/2010 | Gerber et al. |
| 7,853,322 B2 | 12/2010 | Bourget et al. |
| 7,853,329 B2 | 12/2010 | Dilorenzo |
| 7,894,903 B2 | 2/2011 | John |
| 7,899,545 B2 | 3/2011 | John |
| 7,930,035 B2 | 4/2011 | Dilorenzo |
| 7,957,797 B2 | 6/2011 | Bourget et al. |
| 7,957,809 B2 | 6/2011 | Bourget et al. |
| 7,966,073 B2 | 6/2011 | Pless et al. |
| 7,974,696 B1 | 7/2011 | Dilorenzo |
| 8,027,730 B2 | 9/2011 | John |
| 8,126,567 B2 | 2/2012 | Gerber et al. |
| 8,543,214 B2 | 9/2013 | Osorio et al. |
| 8,543,217 B2 | 9/2013 | Stone et al. |
| 8,694,115 B2 | 4/2014 | Goetz et al. |
| 8,706,237 B2 | 4/2014 | Giftakis et al. |
| 8,731,656 B2 | 5/2014 | Bourget et al. |
| 8,903,486 B2 | 12/2014 | Bourget et al. |
| 10,123,717 B2 | 11/2018 | Tcheng |
| 10,252,056 B2 | 4/2019 | Mogul |
| 2003/0018367 A1 | 1/2003 | Dilorenzo |
| 2003/0171789 A1 | 9/2003 | Malek et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0267330 A1 | 12/2004 | Lee et al. |
| 2005/0021103 A1 | 1/2005 | Dilorenzo |
| 2005/0021104 A1 | 1/2005 | Dilorenzo |
| 2005/0060007 A1 | 3/2005 | Goetz |
| 2005/0060008 A1 | 3/2005 | Goetz |
| 2006/0265022 A1 | 11/2006 | John et al. |
| 2007/0073355 A1 | 3/2007 | Dilorenzo |
| 2007/0142862 A1 | 6/2007 | Dilorenzo |
| 2007/0142874 A1 | 6/2007 | John |
| 2007/0162086 A1 | 7/2007 | Dilorenzo |
| 2007/0167991 A1 | 7/2007 | Dilorenzo |
| 2007/0208212 A1 | 9/2007 | Dilorenzo |
| 2007/0287931 A1 | 12/2007 | Dilorenzo |
| 2008/0058773 A1 | 3/2008 | John |
| 2008/0061961 A1 | 3/2008 | John |
| 2008/0071314 A1 | 3/2008 | John |
| 2008/0109005 A1 | 5/2008 | Trudeau et al. |
| 2008/0119900 A1 | 5/2008 | Dilorenzo |
| 2009/0018609 A1 | 1/2009 | Dilorenzo |
| 2010/0023089 A1 | 1/2010 | Dilorenzo |
| 2010/0217348 A1 | 8/2010 | Dilorenzo |
| 2010/0241183 A1 | 9/2010 | Dilorenzo |
| 2010/0249859 A1 | 9/2010 | Dilorenzo |
| 2011/0040353 A1 | 2/2011 | Gerber et al. |
| 2011/0307030 A1 | 12/2011 | John |
| 2016/0228705 A1 | 8/2016 | Crowder et al. |

OTHER PUBLICATIONS

Spencer, S. S., Guimaraes, P., Katz, A., Kim, J., and Spencer, D. Epilepsia: "Morphological patterns of seizures recorded intracranially," 33:537-545 (1992).

Lee, S. A., Spencer, D. D., and Spencer, S. S. Epilepsia: "Intracranial EEG seizure-onset patterns in neocortical epilepsy," 41:297-307 (2000).

Langan, Y., Nashef, L., and Sander, J. W.: "Case-control study of SUDEP," Neurology,64:1131-1133 (2005).

Bateman, L. M., Li, C. S., Lin, T. C., and Seyal, M. Epilepsia: "Serotonin reuptake inhibitors are associated with reduced severity of ictal hypoxemia in medically refractory partial epilepsy," 51:2211-2214 (2010).

Ali Hossam Shoeb: Thesis "Application of Machine Learning to Epileptic Seizure Onset Detection and Treatment", Submitted to Harvard—MIT Div. of Health Sciences re Dr. of Philosophy in EE and Med Engineering at MIT, Sep. 2009.

Maryann D'Alessandro, George Vachtsevanos, Rosana Esteller, Javier Echauz, Stephen Cranstoun, Greg Worrell, Landi Parish and Brian Litt: "A multi-feature and multi-channel univariate selection process for seizure prediction", Clinical Neurophysiology 116 (2005) 506-516.

Isaa Conradsen, Student Member; IEEE, Sándor Beniczky, Karsten Hoppe, Peter Wolf and Helge B. D. Sorensen Member, IEEE: "Automated algorithm for generalised tonic-clonic epileptic seizure onset detection based on sEMG zero-crossing rate", IEEE Transactions on Biomedical Engineering, Copyright IEEE 2011, pubs-permissions@ieee.org.

Alaa Kharbouch, Ali Shoeb, John Guttag, and Sydney S. Cash: "An algorithm for seizure onset detection using intracranial EEG," Epilepsy Balmy. Dec. 2011; 22(01): S29-S35.

Yusuf U Khan, Omar Farooq and Priyanka Sharma: "Automatic Detection of Seizure Onset in Pediatric EEG", International Journal of Embedded Systems and Applications (IJESA) vol. 2, No. 3, Sep. 2012.

Yizhuo Zhang, Guanghua Xu, Jing Wang, Lin Liang: "An automatic patient-specific seizure onset detection method in intracranial EEG based on incremental nonlinear dimensionality reduction", Computers in Biology and Medicine 40 (2010) 889-899. Automated Detection and Quantitative Analysis of Seizures and Short-Term Prediction of Clinical Onset, Epilepsia, 39(6):615-627 (1998).

A.J. Gabor, R.R. Leach, and F.U. Dowla: "Automated Seizure Detection Using a Self-Organizing Neural Network", Dept. of Neurology, University of CA, Davis Medical Center, Jan. 5, 1996; Published Apr. 15, 1996, Electroencephalography and Clinical Neurophysiology 99 (1996) 257-266.

A.J. Gabor: "Automated Seizure Detection Using a Self-Organizing Neural Network", Validation and Comparison with Other Detection Strategies, Dept. of Neurology, University of CA, Davis Medical

(56) References Cited

OTHER PUBLICATIONS

Center, Accepted for Publication Feb. 28, 1998, Electroencephalography and Clinical Neurophysiology 107 (1998) 27-32.
Esteva et al. "Dermatologist level classification of skin cancer with deep neural networks", Nature, vol. 542, published Feb. 2, 2017, pp. 115-118.
Thodoro, M. et al. "Learning Robust Features using Deep Learning for Automatic Seizure Detection", ArXiv:1608.00220, Jul. 31, 2016, pp. 1-12.
Ling, Zhen-Huia et al. "Waveform Modeling and Generation Using Hierarchical Recurrent Neural Networks for Speech Bandwidth Extension", IEEE/ACM Transactions on Audio, Speech, and Language Processing, vol. 26, No. 5, pp. 883-894, May 2018.
Zeiler, Matthew D. et al. "Visualizing and Understanding Convolutional Networks", ArXiv:1311.2901v3, Nov. 28, 2013, pp. 1-11.
Russakovsky et al., "ImageNet Large Scale Visual Recognition Challenge", International Journal of Computer Vision, available online Apr. 11, 2015, published Dec. 2015; vol. 115, Issue 3, DOI 10.1007/s11263-015-0816-; pp. 211-252.
Lecun et al., "Deep Learning", Nature, May 27, 2015, vol. 521; DOI:10.1038/nature14539; pp. 436-444.
Xu et al., "Survey of Clustering Algorithms", IEEE Transactions on Neural Networks, vol. 16, No. 3, May 1, 2005; 35 pages.
Krizhevsky et al., "ImageNet Classification with Deep Convolutional Neural Networks", NIPS'12 Proceedings of the 25th International Conference on Neural Information Processing Systems—vol. 1, pp. 1097-1105, Dec. 3, 2012.
Desai, Sharanya, "Insights from mining large-scale human EcoG data", ICTAL2017, The Penumbra Conference, presented Aug. 21, 2017.
Desai et al., "Deep Learning for seizure classification and potential seizure biomarker discovery", Abstract, published online at www.aesnet.org on Nov. 20, 2017.

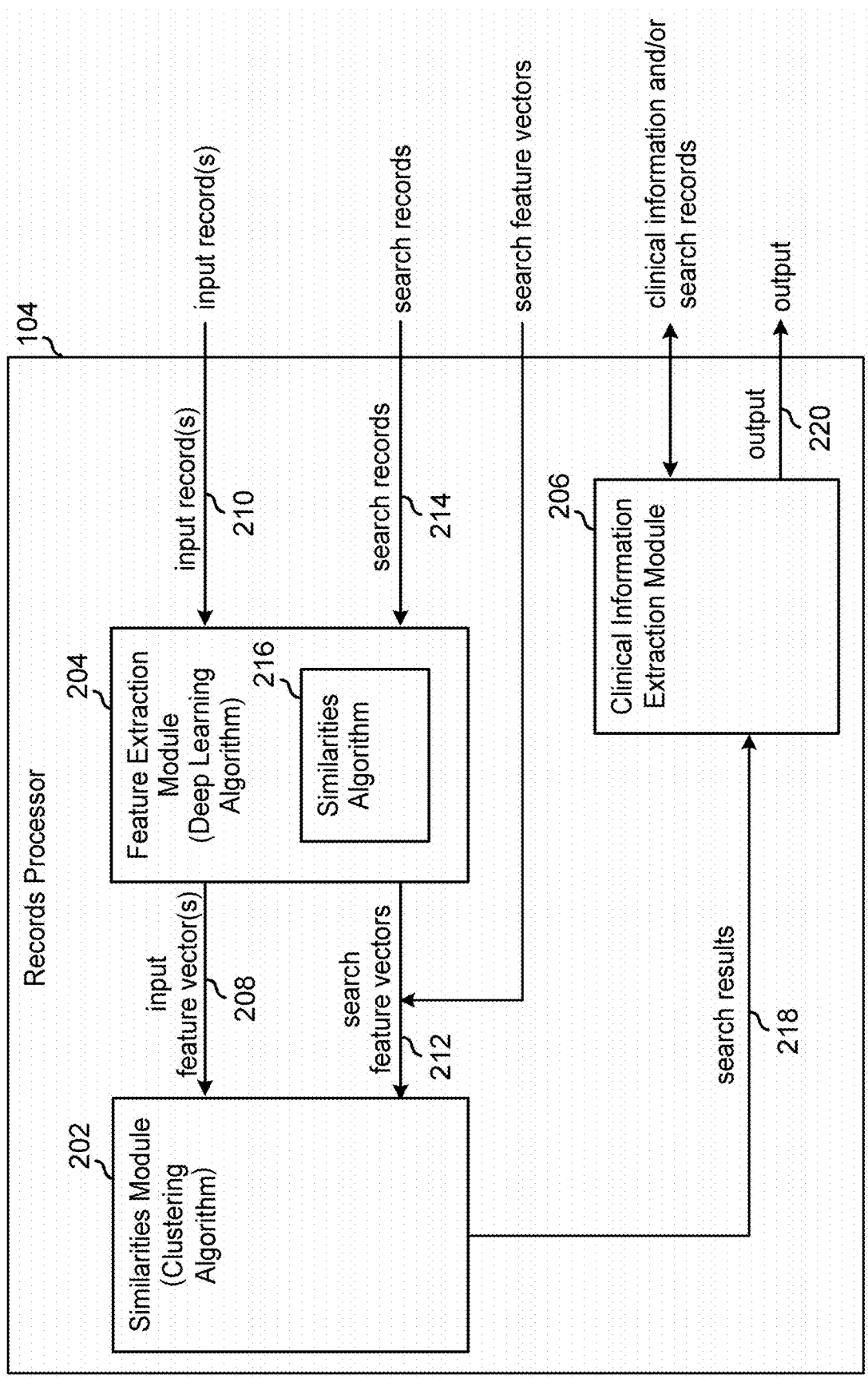

| | Similarity Index table. Patients are sorted by Similarity Index (smaller distance value = higher similarity) | | | | | |
|---|---|---|---|---|---|---|
| Input ECoG record number | Patient ID | Distance metric | Patient ID | Distance metric | Patient ID | Distance metric |
| 1 | 30 | 8 | 42 | 8.5 | 43 | 8.6 |
| 2 | 42 | 9 | 99 | 9.3 | 145 | 9.7 |
| 3 | 12 | 7 | 40 | 9.2 | 30 | 9.3 |

802 → row 1
804 → row 2
806 → row 3

FIG. 8A

| Cumulative rank of patients | Patient ID | Number of time patients appeared in top positions in similarity Index table | Average distance |
|---|---|---|---|
| 1 | 30 | 2 | 8.65 |
| 2 | 42 | 2 | 8.75 |
| 3 | 12 | 1 | 7 |
| 4 | 43 | 1 | 8.6 |
| 5 | 40 | 1 | 9.2 |
| 6 | 99 | 1 | 9.3 |
| 7 | 145 | 1 | 9.7 |

FIG. 8B

SYSTEMS AND METHODS FOR CLINICAL DECISION MAKING FOR A PATIENT RECEIVING A NEUROMODULATION THERAPY BASED ON DEEP LEARNING

CROSS-REFERENCE TO RELATED APPLICATIONS

This application is a continuation application of U.S. patent application Ser. No. 15/849,492, filed Dec. 20, 2017, entitled "Systems and Methods for Clinical Decision Making for a Patient Receiving a Neuromodulation Therapy Based on Deep Learning," which claims the benefit of U.S. Provisional Application Ser. No. 62/575,351, also entitled "Systems and Methods for Clinical Decision Making for a Patient Receiving a Neuromodulation Therapy Based on Deep Learning," and filed on Oct. 20, 2017, each of which is expressly incorporated by reference herein in its entirety.

TECHNICAL FIELD

The present disclosure relates generally to systems and methods for clinical decision making for a patient using data from the patient and data from other patients, and more particularly, to systems and methods that apply deep learning algorithms to data corresponding to electrical activity of the patient's brain, to identify information relevant to making clinical decisions for the patient.

BACKGROUND

Patients with neurological disorders, such as epilepsy, may be treated with one or more forms of neuromodulation therapy, including for example, electrical neurostimulation therapy and drug therapy. Electrical neurostimulation may be delivered by an implanted neurostimulation system that is configured to detect neurological events, such as seizures or seizure onsets, and to generate and deliver a form of electrical neurostimulation to the brain in response to such detections. The neurostimulation system detects neurological events and generates a form of neuromodulation in accordance with a set of detection parameters and a set of stimulation parameters. For example, the neurostimulation system can be configured to deliver electrical stimulation in response to detection of a neurological event. An example of a responsive neurostimulation system is described in U.S. Pat. No. 6,480,743, entitled "System and Method for Adaptive Brain Stimulation," the disclosure of which is herein incorporated by reference.

A clinician may adjust either or both parameters that govern which patterns or other conditions comprise "events" and the parameters that govern what form of neurostimulation therapy is generated and provided in an effort to tailor the therapy for each patient. The clinician likewise can adjust a drug therapy the patient is receiving at the same time as the neurostimulation therapy to optimize a patient's overall treatment outcome. With respect to the responsive neurostimulator, there are many different parameters that govern detection, on the one hand, and stimulation, on the other. Moreover, there is a range of possible values for each parameter. With respect to drug therapy, variations in type of drug, dose of drug, and time of dose are all adjustable variables. While there may be commonality among patients with respect to a given disorder or condition (such as epilepsy) in some respects, detection and therapy need to be tailored for individuals to achieve optimal outcomes. Adjusting the multiple parameters to fine tune the values for each patient can be time consuming. Clinicians with a lot of experience with neurostimulation systems may be able to rely on experience or published research to inform decisions, but the process of optimizing therapy still is typically iterative and can take a long time, driven in part by how often the patient is seen at an office visit. Conventional computer systems used by clinicians for purposes of optimizing neuromodulation therapy typically store historical data for a patient, including for example the patient's medical history, past and present values for the patient's detection parameters and stimulation parameters and drug regimen parameters, and corresponding patient outcome metrics regarding the success or lack thereof, of a neurostimulation therapy or drug therapy. These conventional computer systems simply provide clinician access to a particular patient's data, through visual display or printed reports, which the clinician may use in combination with her experience to inform clinical decisions regarding neuromodulation therapy for that patient. The patient's data, however, is presented in a vacuum so to speak, in that the computer system's storage and presentation of the patient's data does not account for the data of other similarly situated patients.

Deep learning is an advanced machine learning technique which automates the process of feature extraction from training datasets. In traditional machine learning, a human pre-processes training datasets, extracts features from the training datasets, selects best features iteratively, and trains an algorithm which uses the extracted features to train classification, regression, or clustering algorithms. In deep learning, the manual feature extraction and selection steps can be eliminated and the training algorithm automatically performs these steps as part of a model optimization process. Deep learning algorithms require an amount of data for training which is several orders of magnitude greater than the amount of data for training that is required by less advanced machine learning algorithms. Deep learning algorithms additionally provide very little insight into the features extracted for training. Despite these limitations, deep learning has led to impressive advancements in the fields of computer vision and natural language processing. For example, the automated feature extraction and selection steps in deep learning algorithms have played a big role in exceeding performance metrics set by traditional machine learning algorithms in computer vision classification competitions. One such competition is described in ImageNet Large Scale Visual Recognition Challenge, by Olga Russakovsky, Jia Deng, Hao Su, Jonathan Krause, Sanjeev Satheesh, Sean Ma, Zhiheng Huang, Andrej Karpathy, Aditya Khosla, Michael Bernstein, Alexander C. Berg, and Li Fei-Fei. International Journal of Computer Vision, available online Apr. 11, 2015, paper publication December 2015, Volume 115, Issue 3, pp 211-252.

It is desirable to provide for more efficient and automated determination of optimal therapy parameters for a patient receiving a form of neuromodulation therapy. To this end, the concepts disclosed below include a deep learning based system and method that identifies information relevant to making clinical decisions for a patient, including neurostimulation therapy parameter values, for the patient based on electrical activity of the patient's brain and electrical activity of other patients' brains.

SUMMARY

A system identifies information of other patients, which may be relevant to a subject patient, using electrical activity records ("EEG records") of the patient's brain and EEG records of other patients' brains, as well as other information about each patient, maintained in a database. The other information about each patient in the database can be of any nature and type, and may include, for example, clinical information about what therapy(ies) each patient is receiving or has received, and whether a given therapy or combination of therapies is or has been effective for the patient. Preferably, the EEG records and other information in the database corresponds to a large patient population.

A records processor implements a deep learning algorithm on EEG records stored in the database to obtain at least one input feature vector for a patient of interest (the "subject patient") together with a set of search feature vectors. The input feature vector includes a plurality of different features extracted by the deep learning algorithm from an EEG record of the subject patient ("input EEG record"), while each search feature vector in the set of search feature vectors includes a plurality of different features extracted by the deep learning algorithm from the EEG records of other patients ("search EEG records"). A similarities algorithm, such as a k-nearest neighbors algorithm or a K-means clustering algorithm, is applied to the input feature vector and the search feature vectors to identify a subset of search EEG records having a measure of similarity with the input EEG record ("similar search EEG records").

In addition to identifying the similar search EEG records, the system identifies information in the database that is associated with each patient to whom a similar search EEG record belongs. The system then makes both the similar search EEG records and the identified information available to the clinician (e.g., via a user interface display). The clinician can use the identified information to inform decisions intended to optimize the subject patient's outcome with a therapy (e.g., by adjusting the value of a parameter that governs delivery of an instance of electrical stimulation and/or by changing the time of day at which the subject patient takes a dose of a drug).

The identified information may benefit the subject patient, for example, because it may reveal parameter values that were effectively used in therapy for one of the other patients that may also lead to a desired outcome for the subject patient. For example, the clinician may refer to the identified information in deciding whether to adjust the settings that determine how the subject patient receives a therapy or therapies. For example, when the subject patient and the other patients are being treated with an implanted neurostimulation system that delivers electrical stimulation therapy in response to detecting an event in a sensed EEG signal, the identified information may include the values to which the detection parameters and the stimulation parameters are set in the implanted neurostimulation systems of the other patients at a time when the other patients demonstrated a favorable response to the therapy (e.g., a reduction in electrographic seizures and/or a reduction in clinical seizures as reported by the patient). Based on this information, the clinician may decide to reprogram the subject patient's neurostimulator with the detection parameter settings and stimulation parameter settings being used with the other patient. Alternatively, a system may execute algorithms in addition to the deep learning algorithm to operate autonomously to (1) analyze the identified information associated with the similar search EEG records and (2) determine whether to adjust any of the parameters of the subject patient's therapy(ies) based on the analysis (for example, by instigating reprogramming of the subject patient's implanted neurostimulator), with an option for the clinician to manually override or intervene with respect to the result.

The system thus disclosed improves upon conventional computer systems and processes clinicians use to optimize outcomes for patients being treated with a neurostimulation therapy (alone or in combination with a drug therapy), by leveraging "big data" including records of electrical activity of the brain across a large patient population and related patient information, to quickly arrive at, and present to a clinician, therapy parameter values that are well suited to a subject patient. The data processing and analyses enabled and executed by the system and the outcomes provided thereby, are improvements over the simple "storage and display" processes enabled by conventional computer systems. The system can dramatically truncate a clinician's efforts to find the best therapy parameters for a patient by applying a deep learning algorithm to that large amount of data, by minimizing the extent to which the clinician must rely on trial and error unassisted by the computer—an approach which might never result in the optimal outcome that otherwise might be realized for the patient with the treatment.

It is understood that other aspects of apparatuses and methods will become apparent to those skilled in the art from the following detailed description, wherein various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

Various aspects of apparatuses and methods will now be presented in the detailed description by way of example, and not by way of limitation, with reference to the accompanying drawings, wherein:

FIG. 2 is a block diagram illustration of a records processor included in the system of FIG. 1.

FIGS. 8A and 8B represent an example method of ranking search records included in the search results of a subject patient.

DETAILED DESCRIPTION

Figure 1:
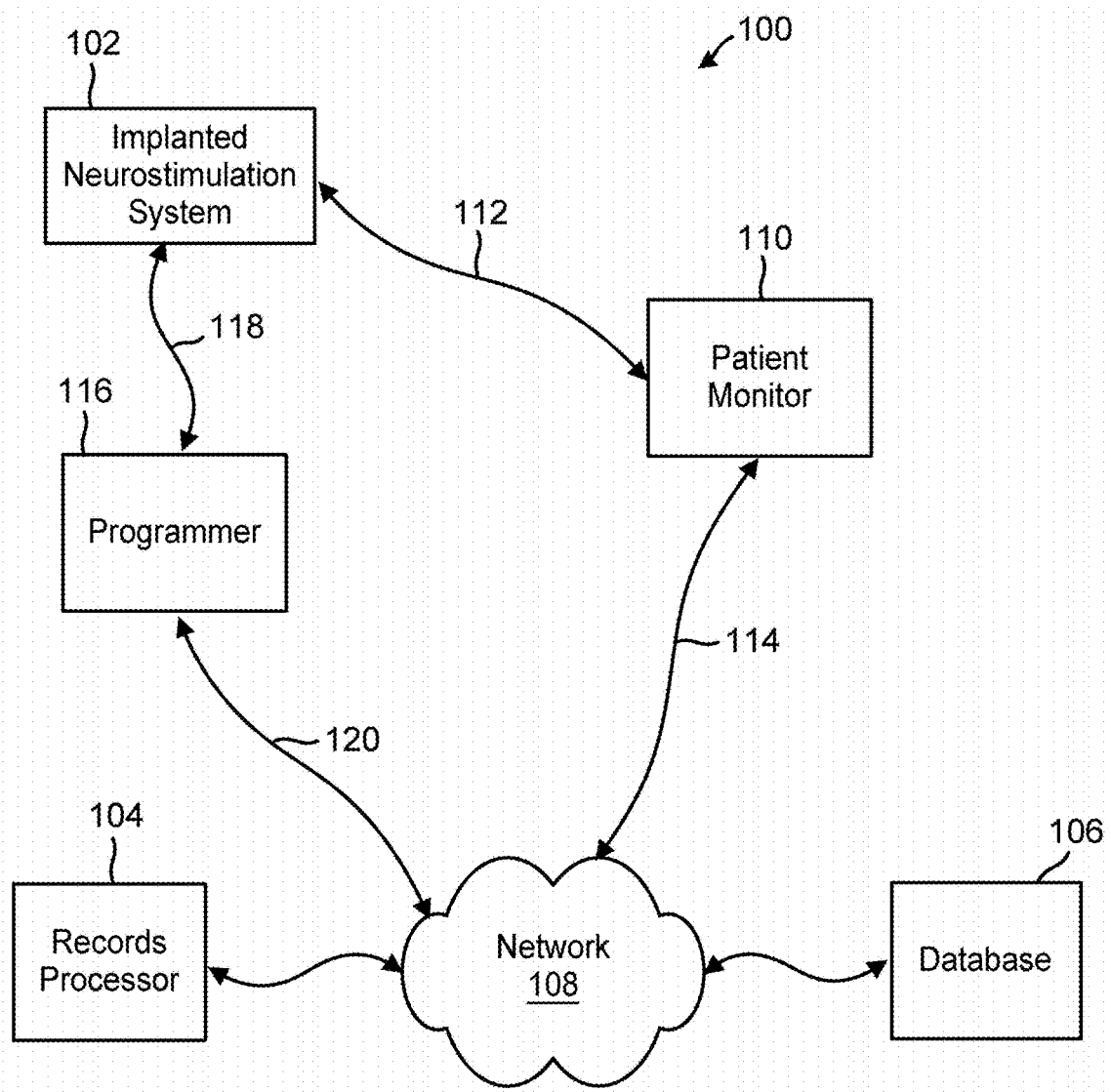
FIG. 1 is a block diagram illustration of a system, including an implanted neurostimulation system, a records processor, and other external equipment, in which deep learning may be applied to electrical activity records of a patient receiving neurostimulation therapy delivered by the implanted neurostimulation system, and electrical activity records of other patients, to identify information useful for decision making by a clinician treating the patient.

Disclosed herein in detail are methods and systems that, for a patient receiving a form of neuromodulation therapy, (1) search for similarities in clinical data corresponding to electrical activity recorded from the subject patient's brain; (2) identify, and in some cases analyze, similar records of electrical activity recorded from other patients' brains; (3) identify clinical information corresponding to the therapy(ies) the other patients are receiving/have received and the outcomes; and (4) use the similar records of electrical activity and the clinical information to inform adjustments to the therapy of the subject patient.

Hereinafter, "EEG" will be used as shorthand to refer to clinical data corresponding to electrical activity of a patient's brain and "EEG records" will be used to refer to recordings of EEGs maintained in the system. It will be understood that "EEG" includes electrical activity sensed directly from the neural tissue, which sometimes is referred to as electrocorticographic activity, an electrocorticogram, or "ECoG". The "clinical information" may be referred to herein as "additional information" or simply as "information" and may include any and all information relating to a patient whose EEG records are used in the disclosed methods and systems. The information may include, without limitation, a patient's clinical response to a therapy (e.g., electrical stimulation) or combination of therapies (e.g., electrical stimulation and drug therapy), medical history (for example, as from a patient's electronic health record or other diagnostic information), history of settings for an active implantable medical device (such as the values of the parameters in a neurostimulator), history of a pharmaceutical (drug) therapy (e.g., type of drug(s), dose of drug, time of delivery of dose), the outcomes or other measure of effectiveness of a given course of treatment or therapy for the patient, and the results of an analysis of data pertaining to the patient, such as an algorithm that classifies the patient's EEG records into one or more types. As used herein, a "neuromodulation therapy" is one that is intended to alter neuronal activity through targeted delivery of a stimulus, such as electrical stimulation or a chemical agent such as a drug, at specific neurological sites in a patient's body.

The identified clinical information may be used, for example, by a clinician to make decisions regarding adjustments or changes to a patient's neuromodulation therapy. Alternatively, the identified clinical information may be used by components of a system to automatically reprogram one or more operational features of the patient's implanted neurostimulation system.

The search and identification operations of the disclosed methods and systems are based on records of electrical activity of the patient's brain and electrical activity of other patients' brains. In general, the method and system rely on a database of EEG records for patients across a patient population, and EEG records of a subject patient. A typical EEG record may correspond to electrical activity of the brain as sensed and recorded by a neurostimulation system. An EEG record may correspond to a digital representation of a time series waveform or an image, such as a spectrogram, of the electrical activity. While the methods and systems herein are primarily described with reference to records comprising brain electrical activity, it will be appreciated that records could also be used that comprise other data, such as measures of other types of physiological activity (e.g., accelerometer recordings, heart rate, blood oxygenation values, neuromodulator concentrations, etc.).

In an example operation of the system, one or more input records corresponding to electrical activity of the subject patient are obtained. For example, a clinician may select one or more input EEG records from the database, which may correspond to one or a few EEG records of the subject patient in a spectrogram form. A set of search EEG records stored in a database and corresponding to EEG records of patients other than the subject patient is also obtained. The obtained search EEG records are of the same type as the input EEG records. For example, if the input EEG record is a spectrogram, then the search EEG records are also spectrograms.

A deep learning algorithm is applied to the input EEG records to obtain an input feature vector that includes a plurality of different features extracted from the input EEG records. The same deep learning algorithm is applied to the set of search EEG records to obtain a corresponding set of search feature vectors, each including a plurality of different features extracted from one of the search EEG records. The deep learning algorithm may be, for example, a convolution neural network, recurrent neural network, or a deep neural network configured to derive features from the input EEG record and the search EEG records. These deep learning algorithms are described in Deep Learning, by Yann LeCun, Yoshua Bengio and Geoffrey Hinton. Nature, published May 27, 2015, Volume 521, pp 436-444. The input feature vector and search feature vector typically each contain thousands of rows, where each row corresponds to a feature extracted from the record by the deep learning algorithm. While the exact nature or characteristics of the features extracted from the EEG records by the deep learning algorithm are not entirely understood, the features are believed to include hierarchically filtered versions of the data forming the record.

A similarities algorithm is then applied to the input feature vector and the search feature vectors to identify a subset of search EEG records having a measure of similarity with the input EEG records. The similarities algorithm may be a k-nearest neighbors algorithm that uses the feature vectors extracted by the deep learning algorithm from the input EEG record as a center point, and identifies the closest search feature vector neighbors to the center point based on a distance calculation between the center point and the neighbors. The closest neighbors to this center point are the EEG records in the set of search EEG records that the similarities algorithm identifies as most like the input EEG record. These similar search EEG records are output as search results. The similarities algorithm may be a clustering algorithm, such as a K-means clustering algorithm. Several clustering algorithms are described in Survey of Clustering Algorithm, by Rui Xu and Donald C. Wunsch, IEEE Transactions on Neural Networks, Institute of Electrical and Electronics Engineers, May 2005.

Once a similar search EEG record is identified, the identity of the patient to whom the search EEG record belongs is known. If information in addition to EEG records exists in the database (or another database) relative to each other patient associated with a search EEG record, then the clinician can call up that information, or the information may be automatically extracted from the database and presented to the clinician. The additional information may comprise, for example, clinical information about the patient's response to a therapy (neurostimulation and/or drug), other aspects of the patient's clinical history, such as past and current neurostimulator parameter settings, and drug therapy information. The clinician may be able to display the similar search EEG records along with this other information in various ways using a user interface connected to the database. In one scenario, the clinician can review the clinical information of the other patients associated with the similar search EEG records and then choose to treat the subject patient with one or more neuromodulation therapies that have been effective for the other patient(s). For example, the clinician may change the value of one or more of the programmable parameters of the subject patient's implanted neurostimulation system to match those used for one of the patients who were identified in the similar search EEG records. Additional information, including the similar search EEG records themselves, may also be extracted from the database and displayed. For example, EEG records in the form of spectrograms may be extracted and displayed.

Having thus provided a general example of a system that identifies relevant clinical information for a patient based on electrical activity of the patient's brain and electrical activity of other patients' brains, a further detailed description of the system follows.

Overview of System

FIG. 1 is a block diagram illustration of a system 100 in which a deep learning algorithm is applied to patient data in the form of EEG records to obtain information useful to clinical decision making for a subject patient. The system includes an implanted neurostimulation system 102, a records processor 104, and a database 106, each configured to provide and/or obtain records of patient data and/or records of clinical information over a network 108.

EEG records are a form of patient data and, in this example, are captured by the implanted neurostimulation system 102. These EEG records may correspond to digitally recorded time series samples of electrocorticographic activity (e.g., a time series waveform). These EEG records may also be in another form or format derived from the time series samples. For example, an EEG record may be a spectrogram image or a time series waveform image of the brain electrical activity. (It will be appreciated that any time-series EEG can be represented as a spectrogram.) Alternatively, time-series waveforms may be directly used.

The neurostimulation system 102 includes implantable components, namely, an active medical device or neurostimulator, and one or more electrode-bearing leads. The electrodes are configured to rest in or on neural tissue in the patient's brain when the leads are implanted. The neurostimulator may be configured to be implanted in or on the patient's cranium or elsewhere in the patient (e.g., pectorally). Once the neurostimulator is implanted, a proximal end of each lead is connected to the neurostimulator. The combination of the active implanted medical device and the implanted lead(s) is configurable to sense physiological signals from the brain, process and store records of the sensed signals, and deliver a form of stimulation to the brain in response to a predefined trigger, such as the detection by the neurostimulator of a predefined condition or neurological event. In this example, the physiological signals the electrodes sense and transmit through the lead(s) to the neurostimulator are electrocorticographic signals. The form of stimulation delivered through the electrodes to the brain tissue is electrical stimulation. The neurostimulator is configured to record samples or segments the sensed EEGs, and to store them in a memory. Once acquired by the neurostimulator, an EEG record can be relayed elsewhere, such as to an external component like the database 106 either directly or through an interim external component. In this example, the patient monitor 110 can be used with an accessory (not shown) to establish a communications link 112 with the implanted neurostimulator (e.g., a short-range telemetry link), which allows EEG records stored on the neurostimulator to be transmitted to the patient monitor 110. Once on the patient monitor, the EEG records can be transmitted to the database 106 via the network 108 (which may comprise a physical 114, WiFi, or cellular internet transmission).

Alternatively, the clinician may be provided with an external component, such as a programmer 116 that, like the patient monitor 110, is configured to establish a communications link 118 with the implanted neurostimulator. The programmer can be used by the clinician to adjust the programmable parameters of the neurostimulator (e.g., the parameters that govern the electrical stimulation waveform that is used for therapy). The programmer also may be used to display the real time EEG signals being sensed by the electrodes from the patient and to store them on the programmer. It also can be used like the patient monitor 110 to acquire EEG records that have been stored by the neurostimulator since the last time the neurostimulator was "interrogated" for those EEG records by either a patient monitor 110 or programmer. As is the case with a patient monitor 110, once EEG records are stored on a programmer, they can be transmitted via the network 108 to other components of the system 100, such as the database 106 and/or the records processor 104 (either directly or via the database 106).

This particular implanted neurostimulation system 102 is configured to deliver electrical stimulation therapy in response to "events" that the neurostimulator is configured to detect. An event may be defined for the neurostimulator by setting the values of programmable detection parameters such that when a pattern corresponding to a pattern defined by the detection parameters occurs in the monitored EEG signals, the occurrence of that pattern will be detected as an event. Other implantable neurostimulation systems that might be used in the subject system may not have this feature of responsive neurostimulation at all or may not have it enabled. The neurostimulator may be programmed to store an EEG record whenever it detects an event (e.g., to store an EEG signal spanning the time period 60 seconds before the event was detected and 30 seconds after). It also can be programmed to store EEG signals at certain times of day (e.g., at noon and at midnight). These are sometimes referred to as "scheduled EEGs." In addition, then neurostimulator may be configured to store an EEG record upon some other trigger, such as when the patient swipes a magnet over the location on the patient's body at which the neurostimulator is implanted (the patient might be instructed to do this whenever he or she thinks a seizure is coming on).

Thus, for a given patient, the database 106 may contain EEG records corresponding to what is happening in the patient's brain in real-time (e.g., as acquired by a programmer), EEG records corresponding to what is happening in the patient's brain during and around when an event occurs, scheduled EEG records acquired at a particular time, and EEG records stored by the neurostimulator when a patient triggers storage with a magnet. Some of these EEG records, especially the ones recorded at the time of an event or when triggered by a magnet swipe, may reflect the patient's electrographic seizures. The database 106 may include information about whatever triggered the neurostimulator to store a given EEG, such as the type of event (e.g., Pattern "A" or Pattern "B", a magnet swipe) or the time of day (e.g., scheduled EEG). The database 106 may accumulate other information acquired from the neurostimulator as well, such as the history of the values used for the programmable parameters of the patient's neurostimulator may be in the database 106 as well, both for detection (if detection is/was enabled) and for stimulation, up to and including the present values for those parameters. Each patient in the database 106 may be associated with an identifier that links each EEG record with a patient or a neurostimulator (e.g., a patient identification number or a medical device serial number). The identifier may be included with each EEG record itself, for example, in a header portion of the digital data sample file that includes the record.

In addition to information acquired from a patient's implanted neurostimulator and lead(s) (neurostimulator-reported information), the database 106 may contain a lot of other information about the patient from a variety of sources, e.g., other databases (electronic health records), data entered by a clinician, and the results of other algorithms run on data about the patient. For example, the patient's clinical history may be in the database, including that history which relates to the condition or disorder that led the patient to have the neurostimulation system 102 implanted in the first place (e.g., epilepsy). The database 106 may include information about drug therapy(ies) to which the patient has been subjected (during or before or after neuromodulation therapy), such as type of drug, dose, and time of day of dose. The patient's clinical response to a form of therapy may also be in the database 106. For example, if the patient has epilepsy, the database may contain patient-reported seizure information, from which a clinician may infer that a patient is having fewer seizures, more frequent seizures, or no appreciable change in seizures. This data may be imported into the database 106 from other sources, such as a patient's electronic health record or personally maintained paper or electronic "seizure diary."

Clinical information about a patient may also be made available to the records processor 104 and/or database 106 by the patient's treating clinician or by the patient herself. For example, during a doctor's visit, the patient may inform the doctor about any changes to health, disease severity which will be updated by the doctor in the patient's clinical information records which is then transmitted to the database. Another example is the doctor may enter information into the records processor 104 that reflects changes to drugs types and dosage prescribed to the patient. The records processor 104 will then transmit the information to the database 106 for storage.

The database 106 may store other information about a patient as the result of other algorithms or computations. For example, an algorithm within the database 106 may be run on the patient's EEG records to classify the EEG records as evidencing an event or condition, such as those evidencing an electrographic seizure or onset of an electrographic seizure, and those evidencing no electrographic seizure activity at all or those considered to comprise a "baseline" condition for the patient.

Clinical information may also be periodically transmitted to the database 106 from a programmer 116 during or soon after a patient follow-up, or anytime a clinician makes changes to the neuromodulation therapy of the patient. Ideally, all the information about a particular patient in the database 106 is maintained to be as current and comprehensive as possible, relative to the reason the patient has the implanted neurostimulation system 102. For example, for any patient actively being treated with the neuromodulation therapy delivered by an implanted neurostimulation system 102, the programmer 116 should be used to transmit current neurostimulator-reported information (stored EEGs, settings for programmable parameters, etc.) to the database 106 at or shortly after the time of a patient visit.

While FIG. 1 illustrates a single implanted neurostimulation system 102 and patient monitor 110 and programmer 116, numerous neurostimulation systems implanted across a patient population may access the network 108 to provide patient EEG records and patient information to the records processor 104 and the database 106. Accordingly, the system 100 can provide access to thousands of patient EEG records and associated information. The system 100 can leverage this vast amount of data to produce and provide information relevant to clinical decision making.

Patient Records and Clinical Information

An aspect of the disclosed system and method depends on the availability of a large amount of patient records for analysis by a deep learning based algorithm. As noted above, the system 100 may collect and store in the database 106, thousands of patient records received from different implanted neurostimulation systems 102 across a patient population, together with corresponding clinical information for each patient.

A patient record in the form of an EEG record represents electrical activity of the brain as sensed by the implanted neurostimulation system 102 corresponding to different times or events or triggers. For example, a neurostimulator can be configured to acquire an EEG when an event the neurostimulator is programmed to detect is detected (and the event may be defined by the neurostimulator's detection parameters to correspond to an electrographic seizure or the onset of an electrographic seizure). It can also be programmed to record an EEG when a patient or caregiver swipes a magnet near the implanted neurostimulator, or at certain times of day or according to a particular schedule. EEGs that do not reflect abnormal activity may be designated as baseline EEG records. The neurostimulator is configured to record an EEG signal as a series of digital data samples, and thus an EEG record typically is transmitted to the database 106 in this format to be stored. The time series of data samples can be used to display the EEG record as a waveform. Each such EEG record also can be transformed (by well-known techniques) into a spectrogram and used in that form. The database can be configured to create an EEG record in the desired form, e.g., time-series waveform or spectrogram, whenever the EEG record is called for by an algorithm (e.g., to display it to a clinician and/or use it in a deep learning algorithm). Alternatively, the EEG records can be created in different formats and stored in those formats at the time they are received into the database 106. Systems and methods disclosed herein may operate on different formats of the EEG recording. For example, a deep learning algorithm may process images (the EEG records as spectrograms). In one circumstance, the system 100 may display EEG records to a clinician as time-series waveforms, and prompt the clinician to select one or more of the EEG records for use as inputs to an instance of the deep learning algorithm. Once the doctor selects some EEG records, the system 100 may convert each selected EEG record to an image before processing them with the deep learning algorithm.

The system and method also depends on the availability of clinical information of patients. As mentioned above, clinical information may include a patient's clinical history, clinical response to neuromodulation therapies, past and current neurostimulation system detection parameter settings and electrical stimulation parameter settings, and past and current drug information. Some or a portion of clinical information may be stored in a neurostimulation system 102 of a patient and periodically transmitted to the database 106. Clinical information may also be transmitted to the database 106 by a clinician through a programmer 116. The record of a patient's clinical information stored in the database 106 includes a patient identifier, which may be in the form of the serial number of the neurostimulation system that provided the clinical information to the database 106 or a patient identification number. As described below, this patient identifier allows for the matching of a patient's clinical information with that patient's records.

Clinical information may be associated with a patient record. For example, each EEG record received from a neurostimulation system may have an associated triggering event that caused the neurostimulation system to record and store the EEG record. For an implanted neurostimulation system, such triggering events may include: 1) detection of abnormal ECoG activity, 2) time of day, or 3) user initiated storage. Clinical information may also be associated with a patient record after it has been transmitted and stored in the database 106. For example, a classification algorithm module associated with the database 106 may process EEG records to determine a classification for the EEG. These EEG classifications may include, e.g., seizure, seizure onset, or baseline. Other types of information include an identifier that links the EEG record with a patient or a neurostimulation system. For example, an identifier of the neurostimulation system that provided the EEG record to the database 106 may be provided in the form of a system serial number or patient identification number. The identifier may be included with the EEG record, perhaps for example, in a header portion of the digital data sample file that includes the record.

Records Processor

Figure 3A:
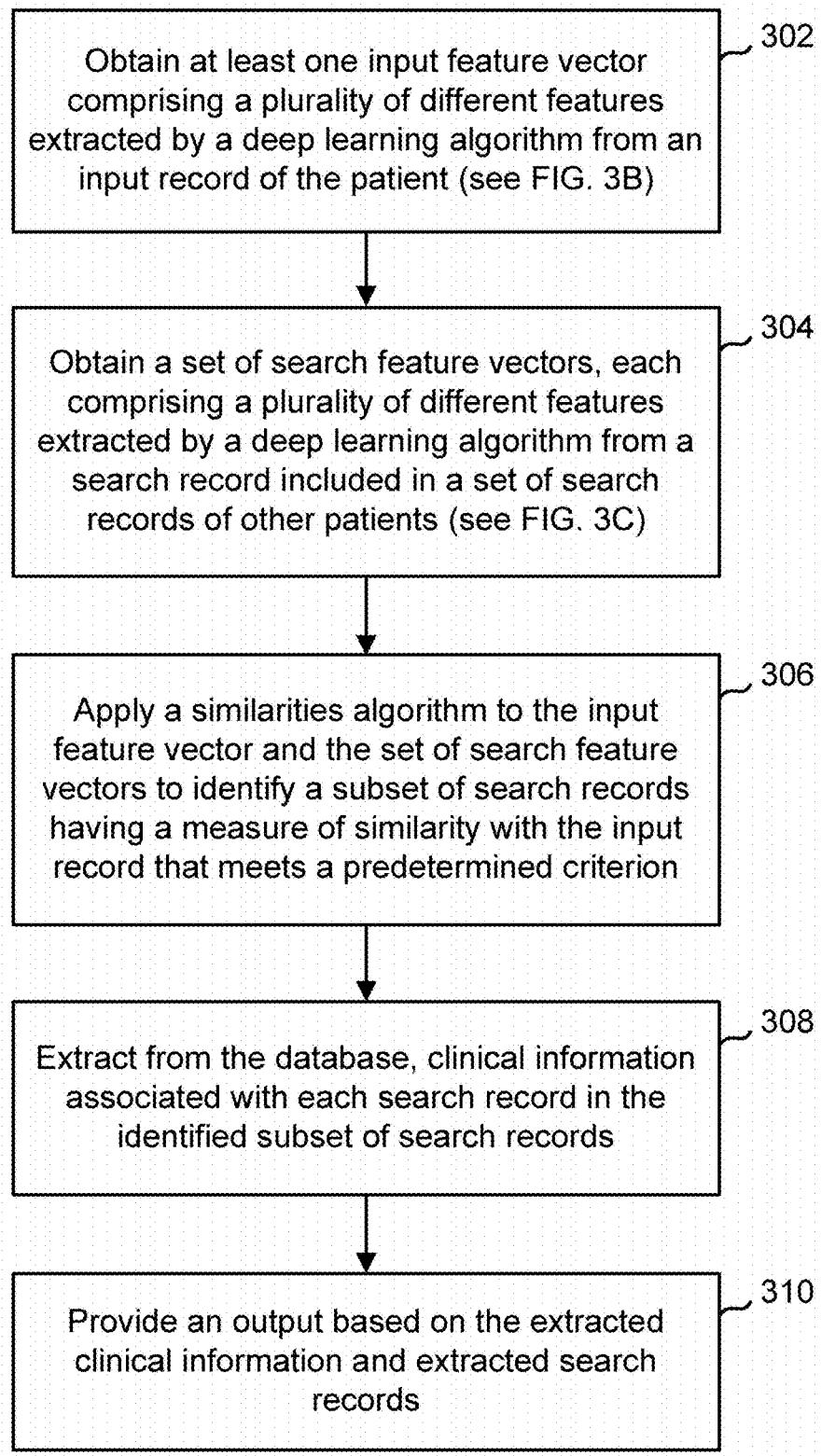
FIGS. 3A, 3B and 3C are flowcharts of methods for identifying information useful for decision making by a clinician treating a subject patient, based on electrical activity records of the subject patient ("input records") and feature vectors derived therefrom, and electrical activity records of other patients ("search records") and feature vectors derived therefrom.
Figure 3B:
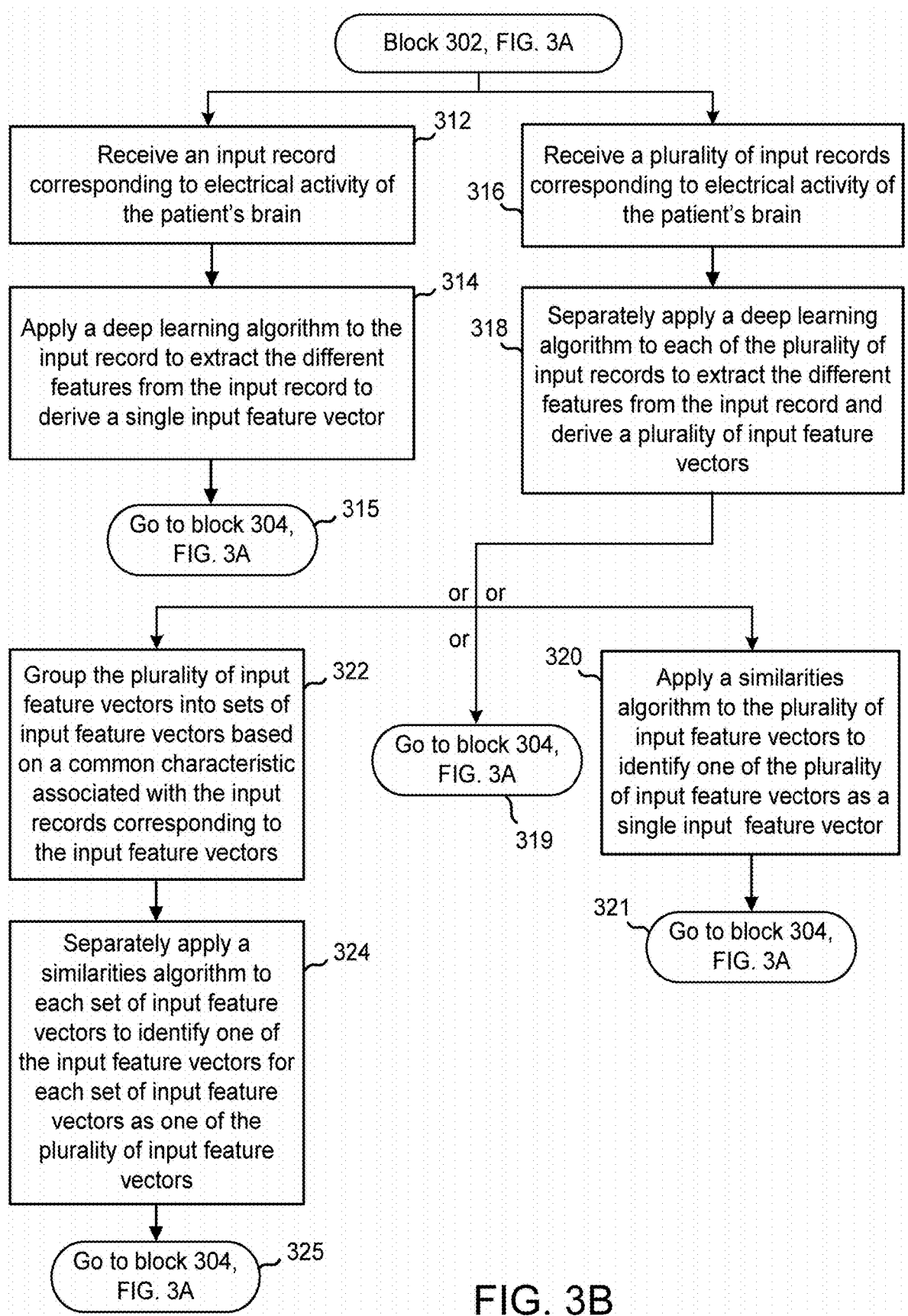
Figure 3C:
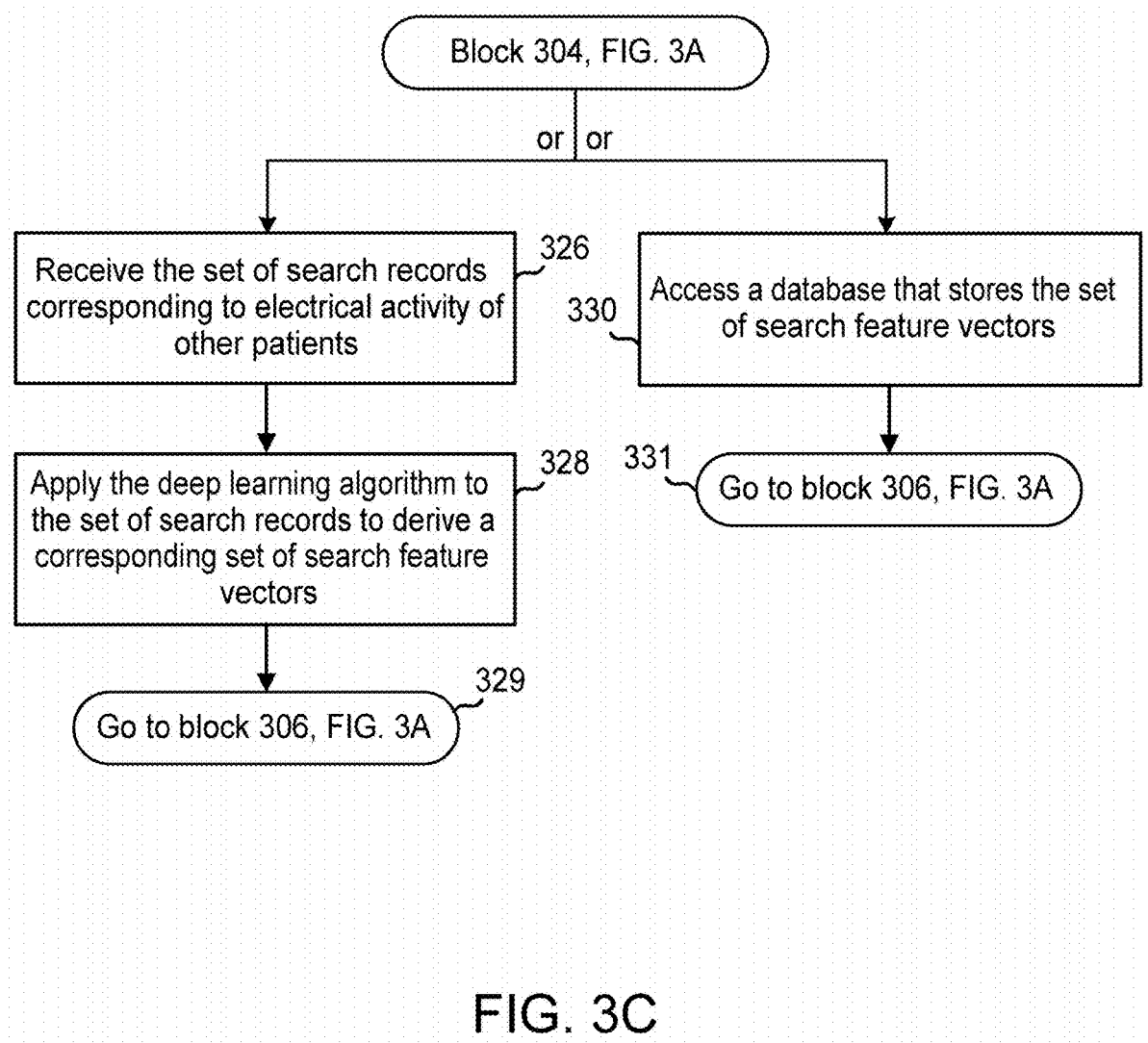

FIG. 2 is a block diagram illustration of a records processor 104 included in the system of FIG. 1. Although shown as a separate component of the system 100 in FIG. 1, the records processor 104 may be included in other system components. For example, the records processor 104 may be included in a programmer 116 or any other computing device included in the system. FIGS. 3A, 3B and 3C are flowcharts of methods for identifying information useful for decision making by a clinician treating a subject patient, based on electrical activity records of the subject patient (referred to herein as "input records") and feature vectors derived therefrom, and electrical activity records of other patients (referred to herein as "search records") and feature vectors derived therefrom. The methods may be performed by the records processor 104, in conjunction with other components of the system 100 of FIG. 1.

In general, the records processor 104 uses a deep learning based algorithm to recognize similarities between one or more input records and a set of search records. The records of the subject patient and the other patients are of the same format, and may for example, be a spectrogram image of an EEG record. A non-exhaustive list of other possible record formats includes a time-series waveform image of an EEG record or a Fourier or wavelet transformed version of the time-series EEG record. Once similarities between an input record and search records are established, the records processor 104 identifies one or more of the search records as a set of search results and extracts clinical information associated with the identified search records, and acts on the extracted clinical information by either providing the information to a user interface or modifying operation of the subject patient's implanted neurostimulation system.

In accordance with the method of FIGS. 3A, 3B and 3C, at block 302, the records processor 104 obtains or derives one or more input feature vectors 208 that includes a plurality of different features extracted from an input record 210 of the patient. Each input feature vector contains thousands of rows, where each row corresponds to a feature extracted from the input record by a deep learning algorithm. Examples of deep learning algorithms that may be employed include convolutional neural networks (CNN), and recurrent neural networks (RNN). The system may also employ pretrained deep learning algorithms, such as AlexNet or Inception-v3; or train the deep learning algorithms from scratch. AlexNet is described in ImageNet Classification with Deep Convolutional Neural Networks, by A. Krizhevsky, I. Sutskever, and G. Hinton, included in Advances in Neural Information Processing Systems 25 (NIPS 2012), available at http://papers.nips.cc/paper/4824-imagenet-classification-with-deep-convolutional-neural-networks. The one or more input feature vectors 208 may be based on a single input record 210 provided to a feature extraction module 204 of the records processor 104, or multiple input records 210 provided to the feature extraction module 204.

In the case of a single input record, at block 312 of FIG. 3B, the feature extraction module 204 of the records processor receives an input record 210. The input record 210 may be received from a programmer 116. For example, a clinician may access through the programmer 116, records of the subject patient that were previously transmitted and stored in the database 106. The clinician may view one or more records of the subject patient and select one of these records as an input record 210 for the feature extraction module 204. After receiving the single input record 210, at block 314 of FIG. 3B, the feature extraction module 204 applies a deep learning algorithm to the input record. The deep learning algorithm is configured to extract the different features from the input record to thereby derive an input feature vector 208. At block 315, the process goes to block 304 of FIG. 3A, where the feature extraction module 204 provides the extracted features to the similarities module 202 in the form of a single input feature vector 208. The operation of the similarities module 202 is described further below.

Continuing for now with FIG. 3B, in instances where multiple input records are involved, at block 316 of FIG. 3B, the feature extraction module 204 receives several input records 210 of the subject patient. This may occur, for example, when a clinician accesses numerous records of the subject patient from the database 106, and selects several of these records as input records for the feature extraction module 204. A clinician may prefer to select multiple input records of the subject patient for processing to include more examples of types of electrical brain activity exhibited by the subject patient. Providing several examples instead of one may be a more robust method for finding similar EEGs.

After receiving multiple input records, the feature extraction module 204 processes the multiple records. To this end, at block 318 of FIG. 3B, the feature extraction module 204 is configured to process each of the multiple input records individually, by separately applying a deep learning algorithm to each of the received input records. The deep learning algorithm is configured to extract the different features from the input record. As an outcome of this multiple processing of the input records, the feature extraction module 204 derives multiple input feature vectors. At this stage, the feature extraction module 204 may further act on the input feature vectors in one of several different ways. In one embodiment, the feature extraction module 204 provides the multiple input feature vectors 208 directly to the similarities module 202. In this case, at block 319 of FIG. 3B, the process returns to block 304 of FIG. 3A.

Figure 4:
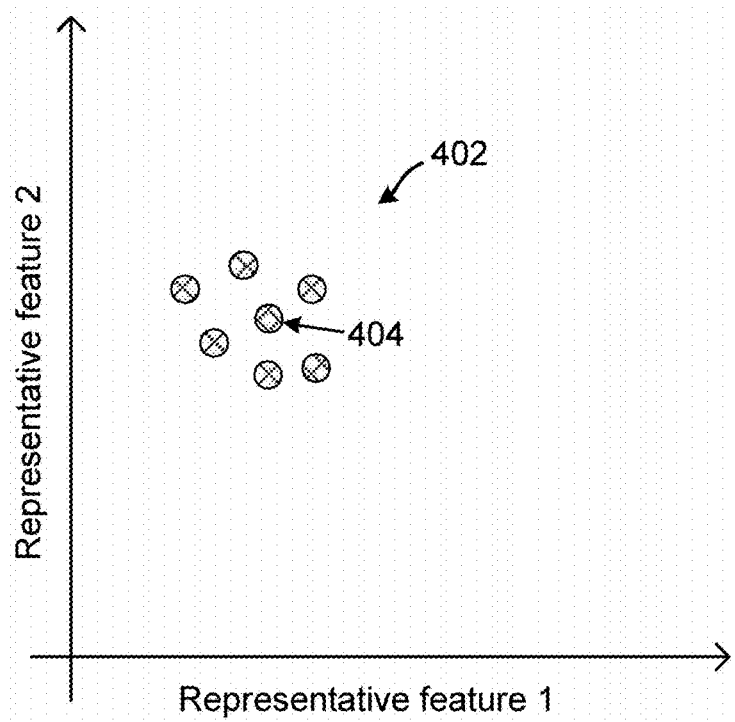
FIG. 4 is a graphical representation of a group of input feature vectors defined by a pair of features extracted by a deep learning algorithm, and an indication of a centroid input feature vector.

In another embodiment, at block 320 of FIG. 3B, the feature extraction module 204 may apply a similarities algorithm 216 to the plurality of input feature vectors. The similarities algorithm 216 is configured to identify one of the plurality of input feature vectors as a single input feature vector and provide the single input feature vector to the similarities module 202. The similarities algorithm 216 may be a clustering algorithm that identifies a centroid of the plurality of input feature vectors. An example operation of the similarities algorithm within this context is provided by FIG. 4, which is a graphical representation of a group of input feature vectors 402 defined by two features extracted by a deep learning algorithm, and an identification of a centroid input feature vector 404 among the group of vectors. The centroid input feature vector 402 is provided to the similarities module 202 as the single input feature vector. Note that in FIG. 4, for clarity of illustration, only two representative features are shown (one along the x-axis and another along the y-axis). Typically, there would be several hundreds or thousands of extracted features. After the similarities algorithm 216 identifies the single input feature vector, at block 321, the process returns to block 304 of FIG. 3A.

In another embodiment, at block 322 of FIG. 3B, the feature extraction module 204 groups the plurality of input feature vectors into sets of input feature vectors based on a common characteristic or piece of information associated with the input records corresponding to the input feature vectors. For example, each input record in a group of input records may have the same associated triggering event that resulted in the input record being stored in the database 106 or the same EEG classification (e.g., seizure, seizure onset, baseline, etc.) as determined by an EEG classification algorithm included in the database or possibly in the feature extraction module 204. Accordingly, the feature extraction module 204 may separate a plurality of input feature vectors into multiple groups or sets of input feature vectors based on a common characteristic. This approach may be taken if saving computation time and power become a priority, or when the clinician selects a large number, e.g., more than 20, of input records. An example EEG classification algorithm that may be employed by the system is described in U.S. Patent Application Publication No. 2016/0228705, entitled "Seizure Onset Classification and Stimulation Parameter Selection," the disclosure of which is herein incorporated by reference.

Next, at block 324, the feature extraction module 204 separately applies a similarities algorithm 216 to each set of input feature vectors to identify a separate one of the input-data features vectors for each set of input feature vectors as one of the plurality of input feature vectors 208. As an outcome of this multiple processing, the feature extraction module 204 provides multiple input feature vectors 208 to the similarities module 202.

Figure 5:
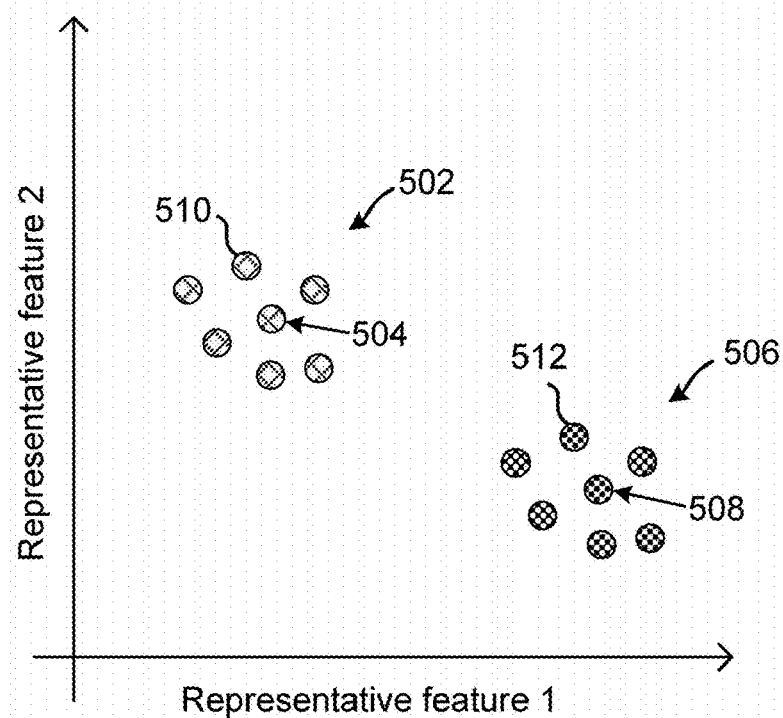
FIG. 5 is a graphical representation of a set of input feature vectors defined by a pair of features extracted by a deep learning algorithm, and an indication of a first centroid input feature vector, and another set of input feature vectors and an indication of a second centroid input feature vector.

An example operation of the similarities algorithm in the context of blocks 322 and 324 is provided by FIG. 5, which is a graphical representation of a first set 502 of input feature vectors defined by a pair of features extracted by a deep learning algorithm, and an identification of a centroid input feature vector 504 among this set of vectors, and a second set 506 of input feature vectors and an identification of a centroid input feature vector 508 among this set of vectors. The input feature vectors 510 in the first set 502 are selected for inclusion in that set based on a common characteristic of their respective underlying input records, i.e., the input record from which the input record vector is derived. Likewise, the input feature vectors 512 in the second set 506 are selected for inclusion in that set based on a common characteristic of their respective underlying input records. As mentioned above, examples of common characteristics include the same trigger event of the underlying input records or the same EEG classification of the underlying input records. The centroid input feature vectors 504, 508 is provided to the similarities module 202 as multiple input feature vectors 208. After the similarities algorithm 216 identifies the input feature vectors, at block 325, the process returns to block 304 of FIG. 3A.

Returning to FIG. 3A, at block 304, in addition to obtaining one or more input data feature vectors as just described, the records processor 104 obtains or derives a set of search feature vectors 212. Each of the search feature vectors in the set of search feature vectors 212 includes a plurality of different features extracted from a search record by a deep learning algorithm. Each search feature vector contains thousands of rows, where each row corresponds to a feature extracted from the data by a deep learning algorithm. The search records from which these search feature vectors are derived are included in a set of search records 214 belonging to patients other than the subject patient. The set of search feature vectors 212 provided to the similarities module 202 may be obtained in various ways.

In one embodiment, the set of search feature vectors 212 is obtained from the feature extraction module 204. In this case, at block 326 of FIG. 3C, the feature extraction module 204 receives a set of search records 214. The set of search records 214 may be obtained by the records processor 104 from the database 106 over the network 108. In one implementation, all available search records are obtained from the database 106. In other implementations, the set of search records may be limited based on additional information associated with the input record. If additional information indicates that the input record represents a seizure event, then the set of search records may be limited to those that also represent seizure events. For example, if the input patient has mesiotemporal lobe seizure onsets, the search records may be records from other patients with mesiotemporal lobe seizure onsets, or in another instance the search records may contain records from all types of seizure onset patients. Likewise, if the input record represents baseline activity, then the set of search records may be limited to those that also represent baseline activity. In yet another implementation, the set of search records may be limited based on the time of recording, so that only the most recently collected search records are selected. For example, the set of search records may be limited to those transmitted to the database in the last month or week or day. The search records may also be limited by a certain range of clinical response associated with the time the records were collected. For example, in the domain of epilepsy, records collected from patients when they had a clinical response of at least 50% reduction in seizures compared to baseline seizure rate may be used as search records.

At block 328, the feature extraction module 204 applies the deep learning algorithm to each search record in the set of search records to derive a corresponding search feature vector for each search record. The result of this individual processing of each search record, is a set of search feature vectors 212. After the feature extraction module 204 identifies the input feature vectors, at block 329, the process returns to block 306 of FIG. 3A.

In another embodiment, at block 330 of FIG. 3C, the set of search feature vectors 212 is obtained by the records processor 104 directly from the database 106. In this case, search feature vectors previously derived by the feature extraction module 204 or a similar module, are maintained in the database 106, and the records processor 104 accesses the database to obtain the stored vectors. After the input feature vectors are obtained, at block 331, the process returns to block 306 of FIG. 3A.

Returning to FIG. 3A, at block 306, a similarities module 202 of the records processor 104 applies a similarities algorithm to the input feature vector(s) 208 and the search feature vectors 212 to identify a subset of search records having a measure of similarity with the input record that meets a predetermined similarity criterion. The similarities algorithm may be a k-nearest neighbors algorithm and the measure of similarity may be a distance between the search records and the input record. More specifically, the similarity may be a measure of the distance between features of the search feature vectors and corresponding features of the input feature vector. The predetermined criterion may be a threshold value of the distance and the subset of search records includes those search records (or search feature vectors) having a distance equal to or less than the threshold value. In an example, the distance may be a Euclidean distance, and the threshold value may be 12.

In cases where a single input feature vector is obtained, a single subset of search records is identified. An example operation of the similarities module 202 in this context is provided by FIG. 6, which is a graphical representation of set of search feature vectors 602, each defined by a pair of features extracted by a deep learning algorithm, and an input feature vector 604 defined by the same pair of features. The similarities module 202 determines the distance between each of the search feature vectors in the set of search feature vectors 602 and the input feature vector 604, and based on these distances identifies a subset of search feature vectors A, B, C as most similar to the input feature vector. Search results 218 are provided to the clinical information extraction module 206. The search results 218 may include an identifier of the sources of the subset of search feature vectors A, B, C. For example, the identifier may be the serial numbers of the neurostimulation systems from which search records were obtained, or corresponding patient identification numbers, either of which can be used to match clinical information in the database with the search results. The search results 218 may also include record numbers that identify each of the search records corresponding to the subset of search feature vectors A, B, C.

Figure 7A:
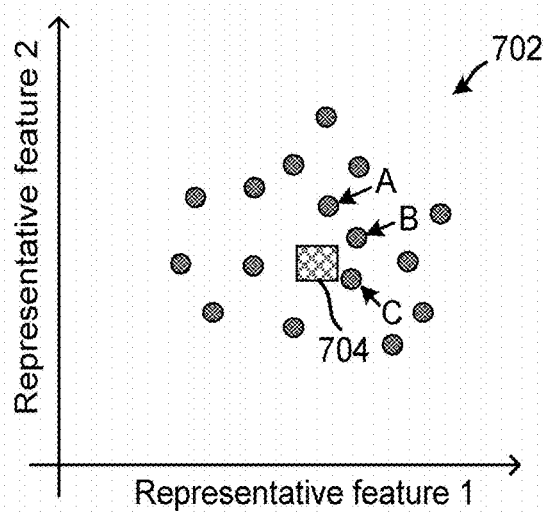
FIGS. 7A and 7B are graphical representations of the same set of search feature vectors, relative to a first input feature vector (FIG. 7A) and a second input feature vector (FIG. 7B), wherein respective subsets of search feature vectors are identified as most like each input feature vector.
Figure 7B:
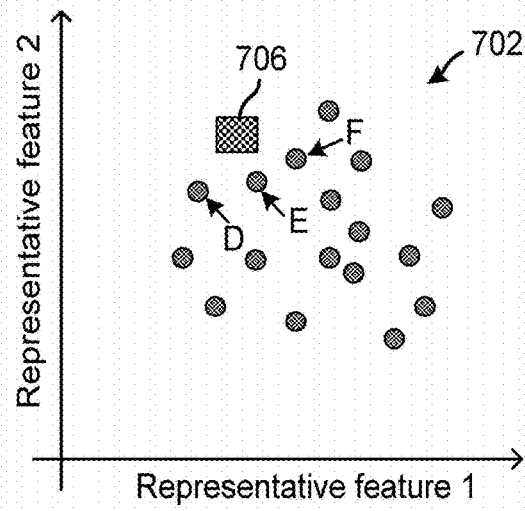

In cases where multiple input feature vectors are obtained, the similarities algorithm is separately applied to each input feature vector, together with the set of search feature vectors, to identify a separate subset of search records for each of the plurality of input records. An example operation of the similarities module 202 in this context is provided by FIGS. 7A and 7B, which are graphical representations of the same set of search feature vectors 702, relative to a first input feature vector 704 (FIG. 7A) and a second input feature vector (FIG. 7B). For each respective input feature vector 704, 706 the similarities module 202 determines the distance between each of the search feature vectors in the set of search feature vectors 702 and the input feature vector. Based on these distances the similarities module 202 identifies a subset of search feature vectors A, B, C as similar to the first input feature vector 704, and a subset of search feature vectors D, E, F as most similar to the second input feature vector 706. Search results 218 are provided to the clinical information extraction module 206. The search results 218 may include an identifier of the sources of the subset of search feature vectors A, B, C, D, E, F. For example, the identifier may be the serial numbers of the neurostimulation systems from which search records were obtained, or corresponding patient identification numbers. The search results 218 may also include record numbers that identify each of the search records corresponding to the subset of search feature vectors.

Returning to FIG. 3A, at block 308, the clinical information extraction module 206 of the records processor 104 processes the search results 218 to extract from the database 106, clinical information associated with each search record identified in the search results 218. To this end, for each identifier, e.g., neurostimulation serial number or patient identifier number, included in the search results 218, the clinical information extraction module 206 searches the database for the clinical information record with a matching identifier. The clinical information extraction module 206 may also process the search results 218 to extract the search records identified by the record numbers included therein. For example, search records in the form of spectrogram images may be extracted from the database 106.

In addition to extracting clinical information and search records, the clinical information extraction module 206 may be configured to rank the search results based on measures of similarity of the search records included in the search results 218. To this end, the search results 218 provided to the clinical information extraction module 206 may further include the similarity measures for each search record. Using this information, the clinical information extraction module 206 may rank the search records identified in the search results from most similar to least similar, relative to the subject patient's input record.

FIGS. 8A and 8B represent an example method of ranking search records included in the search results of a subject patient. With reference to FIG. 8A, in a first part of the ranking process, search results identified by a patient identifier number, are sorted based on a similarity index corresponding to a distance metric. In this example, each row 802, 804, 806 represents a ranking for a different input EEG record of a patient, where each EEG record is identified by an EEG record number. For each input EEG record, the top three search EEG records, as identified by a patient identifier, and corresponding measure of similarity, e.g., distance from subject patient's input record, are determined. The respective search results are ranked in the table of FIG. 8A, from the most similar (lowest distance metric) search record to the least similar search record (highest distance metric). The first part of the ranking process provides a similarity index table like the one shown in FIG. 8A.

With reference to FIG. 8B, in a second part of the ranking process, a cumulative rank is determined based on information included in the similarity index table of FIG. 8A. The ranking shown in FIG. 8B first ranks patients (identified by patient identification numbers) based on the number of times the patients appear in the similarity index table of FIG. 8A. In this example, each of patient 30 and 42 appear twice in the similarity index table of FIG. 8A, while the rest only appear once. If there is a tie based on the frequency of occurrence, as there is in this example, the results are next ranked based on a similarity metric. Continuing with the example of FIG. 8B, based on the distance metrics included in FIG. 8A, respective average distances are determined for each patient. For example, patient 30 appears twice in the table of FIG. 8A, once with a distance of 8 and another with a distance of 9.3. The average distance metric for patient 30 is thus 8.65. A similar calculation for patient 42, who also appears twice in the table of FIG. 8A, results in an average distance of 8.75. Based on these calculations, patient 30 is ranked higher than patient 42 and would thus be identified by the records processor as the best search result for the subject patient.

In the foregoing examples, the search results are described in terms of patients and patient identification numbers. While such description is useful in the sense that it conveys the concept of matching a subject patient with other similar patients for purposes of modifying neuromodulation therapy, from a technical implementation perspective, the system is identifying neurostimulation systems (not patients) that provided search records that appeared in search results. From a practice perspective, a clinician having knowledge of which neurostimulation systems are implanted in which patients would of course be able to match patients with the search results.

Returning to FIG. 3A, at block 310, the clinical information extraction module 206 of the records processor 104 provides an output 220 based on the extracted clinical information and extracted search records corresponding to the search results. In one implementation, the output 220 includes information that enables a user interface to display at least a portion of the extracted clinical information on a display as neuromodulation therapy settings suggestions for the subject patient. The output 220 may be provided to a programmer 116 that is configured to process the output and generate therefrom, on a display of the programmer, text, or graphical representations of some or all the extracted clinical information. For example, the programmer may display past detection parameter settings, past stimulation settings, and past and current drug type and dosage information. The output 220 may also provide the search records corresponding to the search results, in which case the programmer may be configured to display the content of the search record. For example, if the search record is in the format of a spectrogram image, the programmer 116 may display the spectrogram, together with the clinical information. Through the information presented on the display, a clinician may make clinical decisions regarding neuromodulation therapies for the subject patient.

In another implementation, the output 220 includes programming instructions configured to reprogram one or both of the detection parameter settings and the stimulation parameter settings for the patient's implanted neurostimulation system to correspond to the detection parameter settings and the stimulation parameter settings included in the extracted clinical information of one of the search records in the search results. For example, the stimulation settings included in the clinical information associated with the top search result may be selected. In this case, the output 220 may encompass programming instructions that are sent to a programmer 116 over communication link 120. The programmer 116, in turn, may process the programming instructions and autonomously reprogram the settings of the implanted neurostimulation system 102 over communication link 118.

Figure 9:
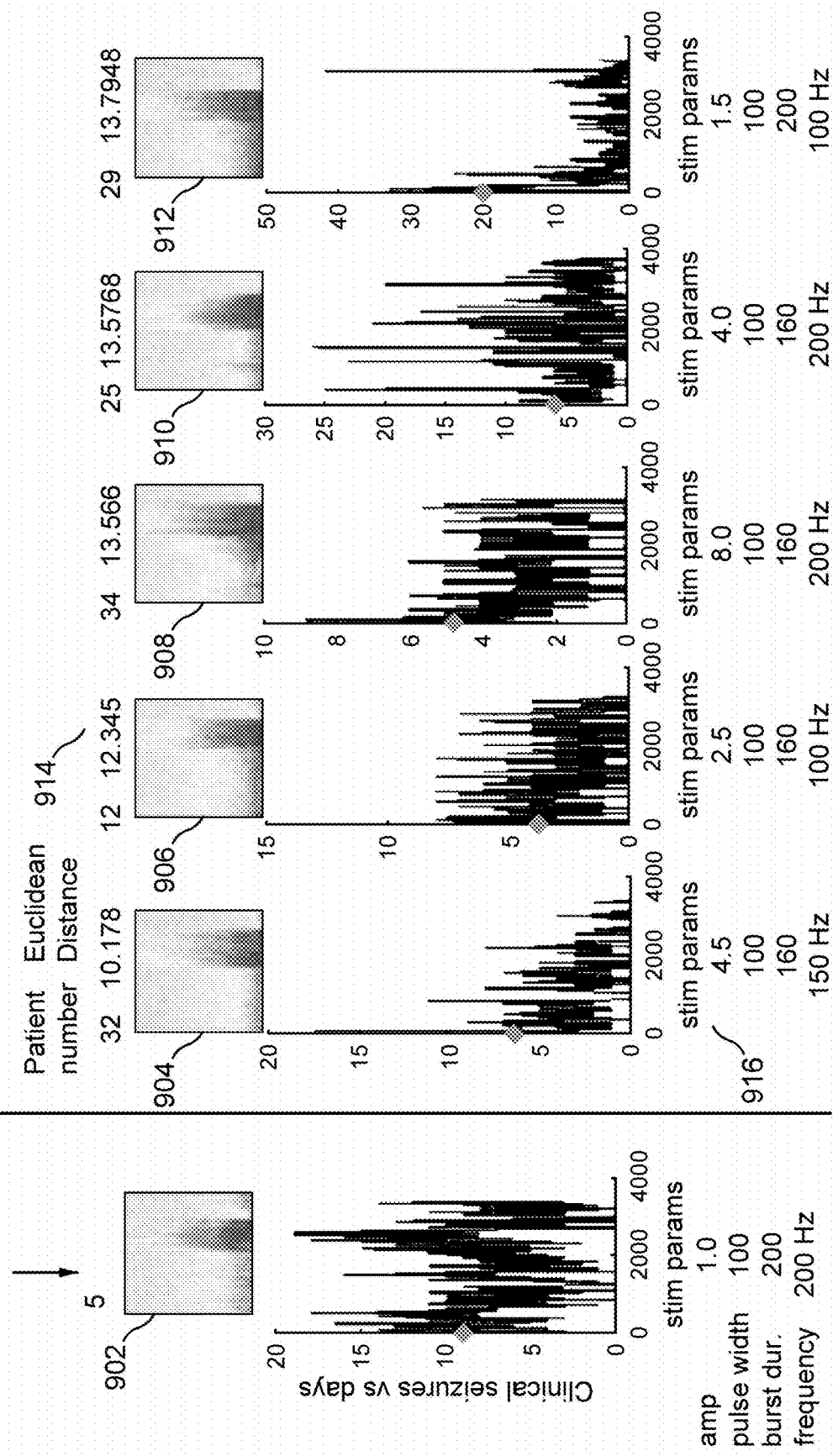
FIG. 9 illustrates example search results of the methods of FIGS. 3A, 3B and 3C, wherein the input record and search records are spectrograms of electrographic seizure activity.

FIG. 9 illustrates a display of the search results of the methods of FIGS. 3A, 3B and 3C, as applied to EEG records in the form of spectrograms of electrographic seizure activity. A single spectrogram 902 is selected as the input record and applied to the records processor 104. Operation of the records processor 104 results in the identification of a number (x) of similar search records 904, 906, 908, 910, 912 that meet a similarity criterion relative to the input record 902. The programmable number (x) may have a default value, but may also be programmed by the clinician. A typical default number is 10 and a typical range of numbers is 1 to 20. In this example, the number (x) is five and the search records consist of spectrogram images.

Figure 6:
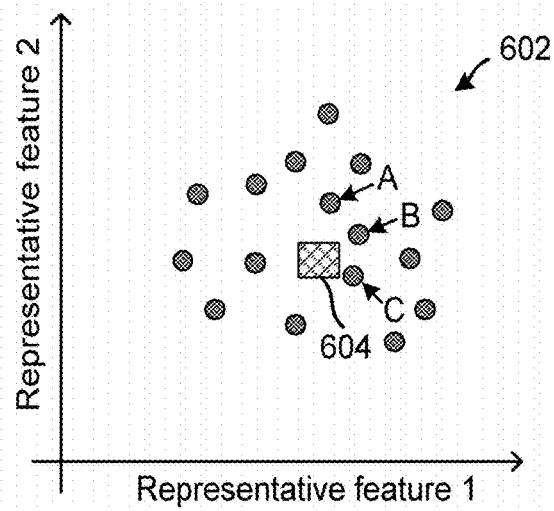
FIG. 6 is a graphical representation of a set of search feature vectors relative to an input feature vector, wherein a subset of search feature vectors is identified as most like the input feature vector.

A measure of similarity 914 is associated with each identified search record in the search results and the records are sorted in order of similarity, with the first displayed spectrogram record 904 having the highest similarity to the input spectrogram 902. Along with displaying spectrogram images, the measure of similarity between the input image and each search-result image, referred to as a similarity index, is displayed for each search record in the search results. In the example of FIG. 9, the measure or index is a Euclidean distance, e.g., 10.178, 12.345, 13.566, etc., between a feature vector representation of the input spectrogram and a feature representation of the search spectrograms, such as shown in FIG. 6. Smaller values of the Euclidean distance indicate closer match between the search spectrogram image and the input spectrogram image.

In some instances, a filter may be applied to limit the number of search records included in the search results. For example, the similarity index may be used as a filter. To this end, the number (x) of records in the search results may be limited using a cutoff applied to the similarity index (such as the Euclidean distance). For example, a cutoff value of 15 for the Euclidean distance may be applied so that only those search records in the search results that have a Euclidean distance <15 from the input spectrogram image are displayed. In another example, a filter may be applied to find only the most similar or the best matching image from each search patient to avoid finding several images from the same patient. Application of this filter will ensure that multiple different patients are identified by the records processor 104. If the clinician chooses not to apply this filter, top matched search records will be displayed irrespective of the patient identification. In this case, several search records in the search results may come from the same patient(s).

Clinical information is associated with each spectrogram record 904, 906, 908, 910, 912 included in the search results. In the example of FIG. 9, the clinical information includes the values of stimulation parameters 916, e.g., amplitude, pulse width, pulse burst duration, and frequency. These parameters 916 are stored in the database 106 and extracted therefrom based on identifiers associated with the underlying EEG records from which the spectrogram records 904, 906, 908, 910, 912 were derived. For each respective spectrogram record 904, 906, 908, 910, 912, the values of the parameters 916 stored in the database and subsequently extracted correspond to the values programmed in the neurostimulation system at the time the underlying EEG records was recorded by that neurostimulation system.

Figure 10:
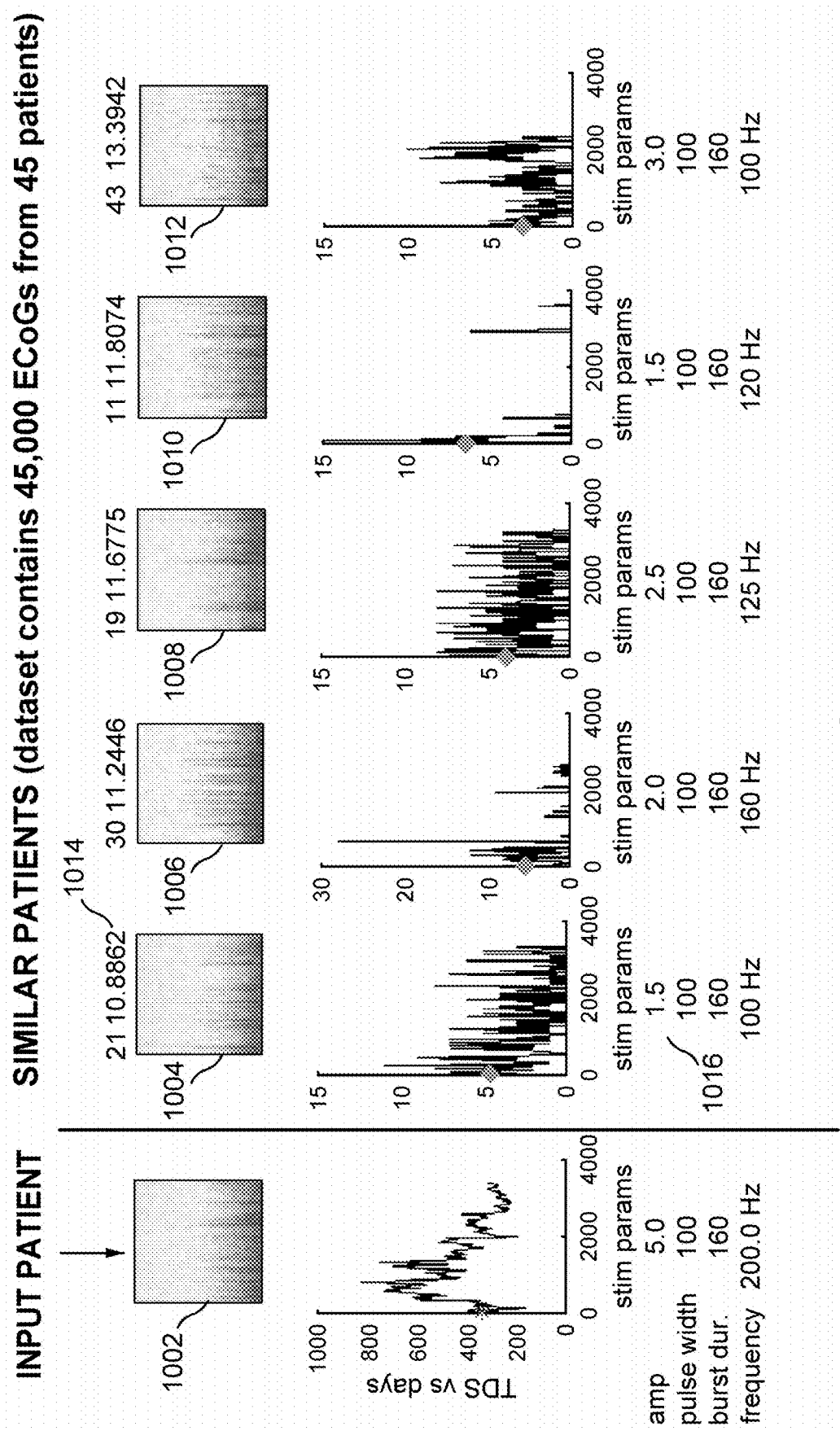
FIG. 10 illustrates example search results of the methods of FIGS. 3A, 3B and 3C wherein the input record and search records are spectrograms of baseline, non-seizure, electrographic activity.

FIG. 10 illustrates a display of the search results of the methods of FIGS. 3A, 3B and 3C, as applied to records in the form of spectrograms of baseline, non-seizure electrographic activity. A single spectrogram 1002 is selected as the input record. Operation of the records processor 104 results in the identification of spectrogram search records 1004, 1006, 1008, 1010, 1012 that meet a similarity criterion relative to the input record 1002. A measure of similarity 1014 is associated with each identified search record. In the example of FIG. 10, the measure is a Euclidean distance between a feature vector representation of the input spectrogram and a feature representation of the search spectrograms, such as shown in FIG. 6. Clinical information is associated with each spectrogram search record 1004, 1006, 1008, 1010, 1012 in the search results. In the example of FIG. 10, the clinical information is the values of stimulation parameters 1016 currently programmed in the neurostimulation system from which the respective spectrogram search record 1004, 1006, 1008, 1010, 1012 was obtained.

Having thus described the configuration and operation of a system 100 including a records processor 104 that searches for and identifies relevant clinical information for a patient through deep learning, an overview of an example implanted neurostimulation system that may be included in the system is provided.

Overview of Implanted Neurostimulation System

Figure 11:
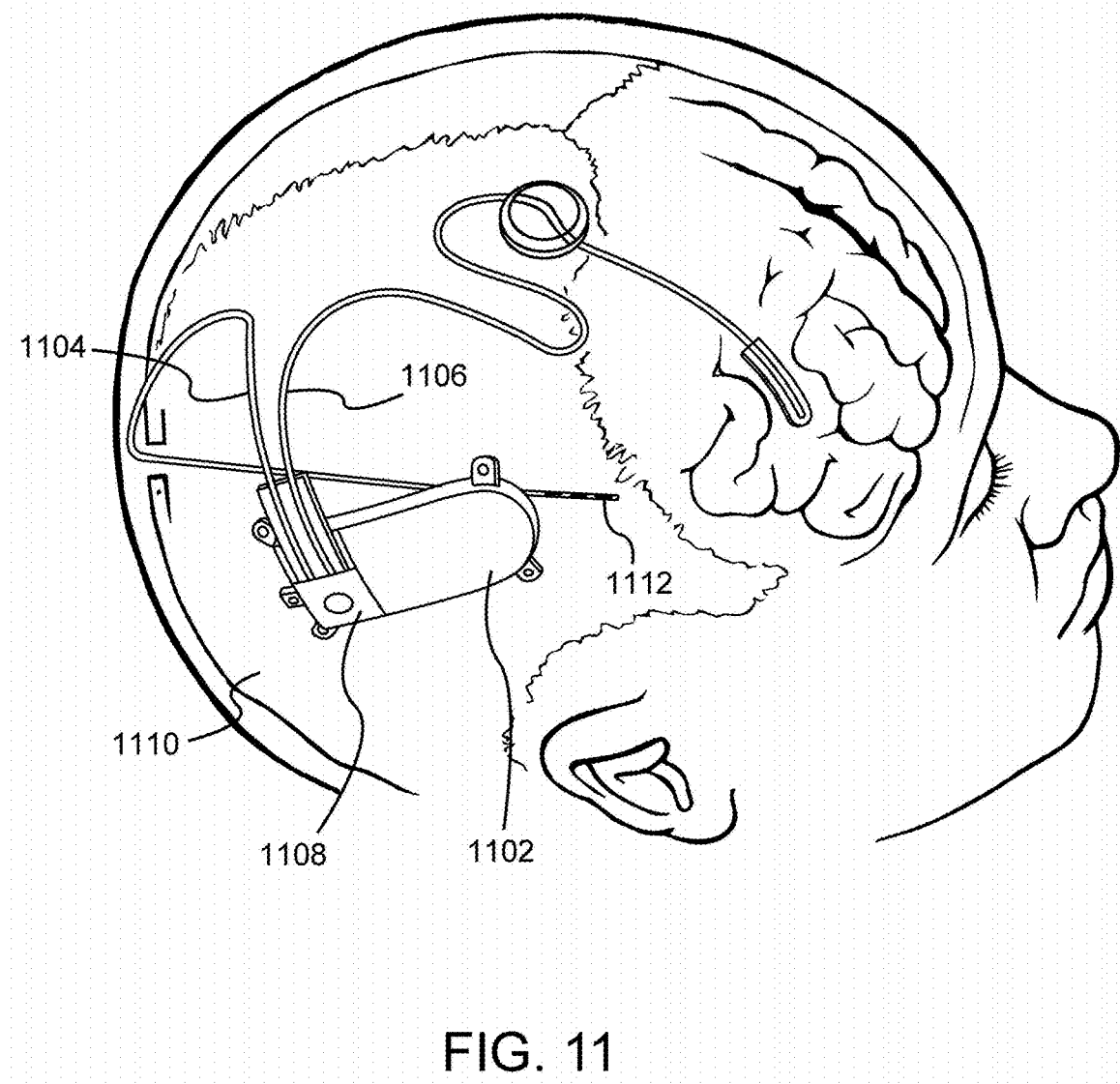
FIG. 11 is a perspective, schematic illustration of an implanted neurostimulation system implanted in a patient and configured to sense and record electrical brain activity and provide such records as part of the system of FIG. 1.

FIG. 11 is an illustration of the implanted neurostimulation system including an active neurostimulator 1102 and two electrode-bearing brain leads 1104, 1106, implanted in a patient. The system is configured to sense and record electrical brain activity and provide such records as part of the system of FIG. 1.

The neurostimulator 1102 includes a lead connector 1108 adapted to receive one or more of the brain leads, such as a deep brain or depth lead 1104 and a cortical strip lead 1106. The depth lead is implanted so that a distal end of it is situated within the patient's neural tissue, whereas the cortical strip lead is implanted under the dura mater so that a distal end of it rests on a surface of the brain. The lead connector 1108 acts to physically secure the brain leads 1104, 1106 to the neurostimulator 1102, and facilitates electrical connection to conductors in the brain leads 1104, 1106 coupling one or more electrodes at or near a distal end of the lead to circuitry within the neurostimulator 1102.

The proximal portion of the deep brain lead 1104 is generally situated on the outer surface of the cranium 1110 (and under the patient's scalp), while the distal portion of the lead enters the cranium 1110 and is coupled to at least one depth electrode 1112 implanted in a desired location in the patient's brain. The proximal portion of the cortical lead 1106 is generally situated on the outer surface of the cranium 1110 (and under the patient's scalp), while the distal portion of the lead enters the cranium 1110. The distal portion of the cortical lead 1106 includes at least one cortical electrode (not visible) implanted in a desired location on the patient's brain.

Figure 12:
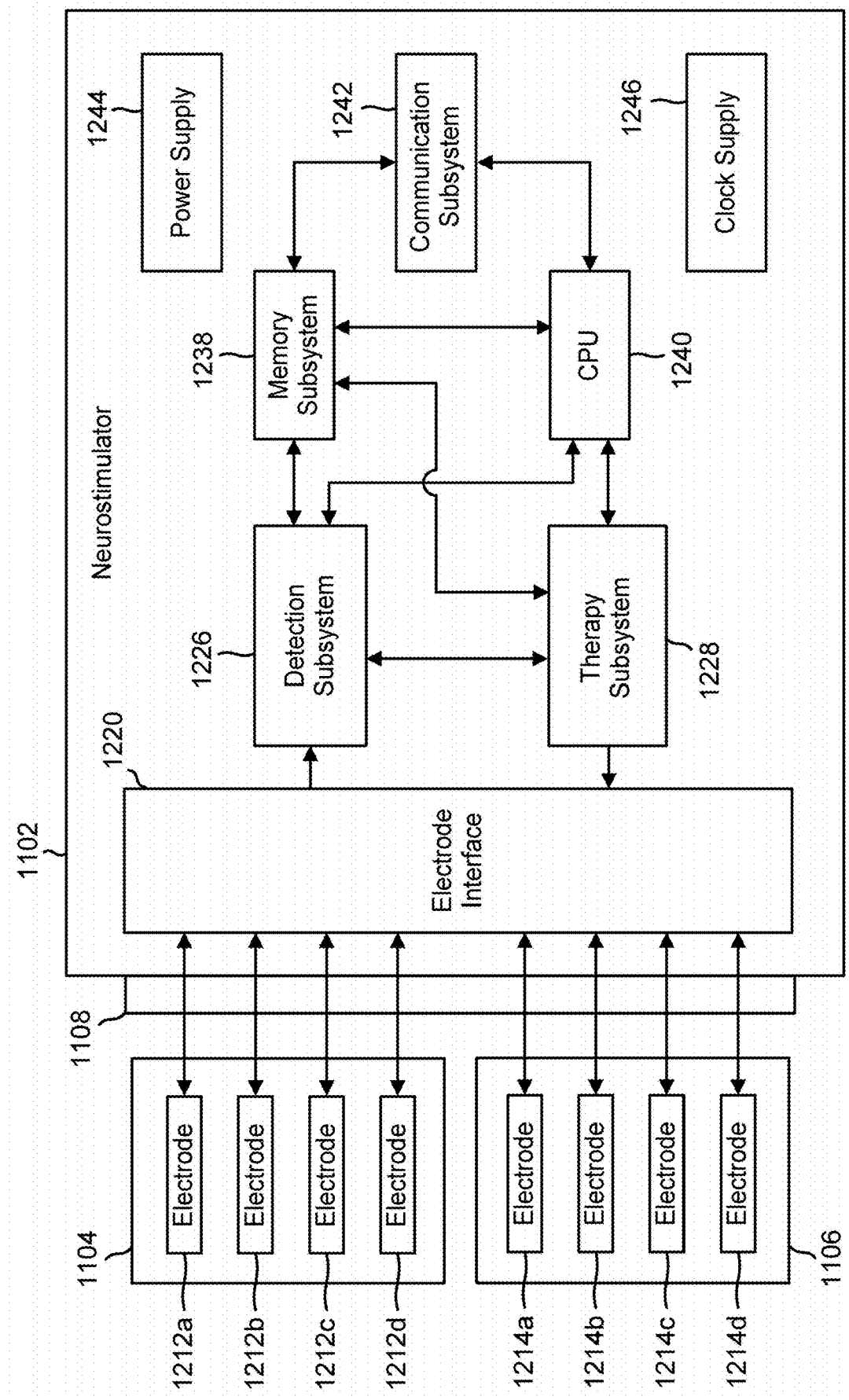
FIG. 12 is a block diagram of the implanted neurostimulation system of FIG. 11, illustrating some of the functional subsystems of the system.

FIG. 12 is a block diagram of the implanted neurostimulation system of FIG. 11. The system may be configured to sense electrical brain activity, detect neurological events in accordance with a set of detection parameters, delivery electrical neurostimulation to the brain in accordance with a set of stimulation parameters, and store records of electrical brain activity for transmission to the database 106 of the system of FIG. 1.

The neurostimulator 1102 includes a lead connector 1108 adapted to receive a connector end of each brain lead 1104, 1106, to thereby electrically couple each lead and its associated electrodes 1212a-d, 1214a-d with the neurostimulator. The neurostimulator 1102 may configure an electrode 1212a-d, 1214a-d as either a sensor (for purposes of sensing electrical activity of the brain) or a stimulator (for purposes of delivering therapy to the patient in the form of electrical stimulation) or both.

The electrodes 1212a-d, 1214a-d are connected to an electrode interface 1220. The electrode interface 1220 can select each electrode 1212a-d, 1214a-d as required for sensing and stimulation. The electrode interface 1220 may also provide any other features, capabilities, or aspects, including but not limited to amplification, isolation, and charge-balancing functions, that are required for a proper interface with neurological tissue. The electrode interface 1220 is coupled to a detection subsystem 1226, which is configured to process electrical activity of the brain sensed through the electrode 1212a-d, 1214a-d. The electrode interface 1220 may also be coupled to a therapy subsystem 1228, which is configured to deliver therapy to the patient through the electrode 1212a-d, 1214a-d in the form of electrical stimulation.

The neurostimulator 1102 includes a memory subsystem 1238 and a central processing unit (CPU) 1240, which can take the form of a microcontroller. The memory subsystem 1238 is coupled to the detection subsystem 1226, and may receive and store records of data representative of sensed electrographic signals for transmission to the system of FIG. 1. The memory subsystem 1238 is also coupled to the therapy subsystem 1228 and the CPU 1240. In addition to the memory subsystem 1238, the CPU 1240 is also connected to the detection subsystem 226 and the therapy subsystem 1228 for direct control of those subsystems.

The neurostimulator 1102 also includes a communication subsystem 1242. The communication subsystem 1242 enables communication between the neurostimulator 1102 and an external device, such as a programmer 116 or patient monitor 110, through a wireless communication link. As described above with reference to FIG. 1, the programmer 116 allows a clinician to read out records of patient data, as well as ancillary information associated with those records. The neurostimulator 1102 also includes a power supply 1244 and a clock supply 1246. The power supply 1244 supplies the voltages and currents necessary for each of the other subsystems. The clock supply 1246 supplies substantially all the other subsystems with any clock and timing signals necessary for their operation.

Overview of Computing Device with Records Processor

Figure 13:
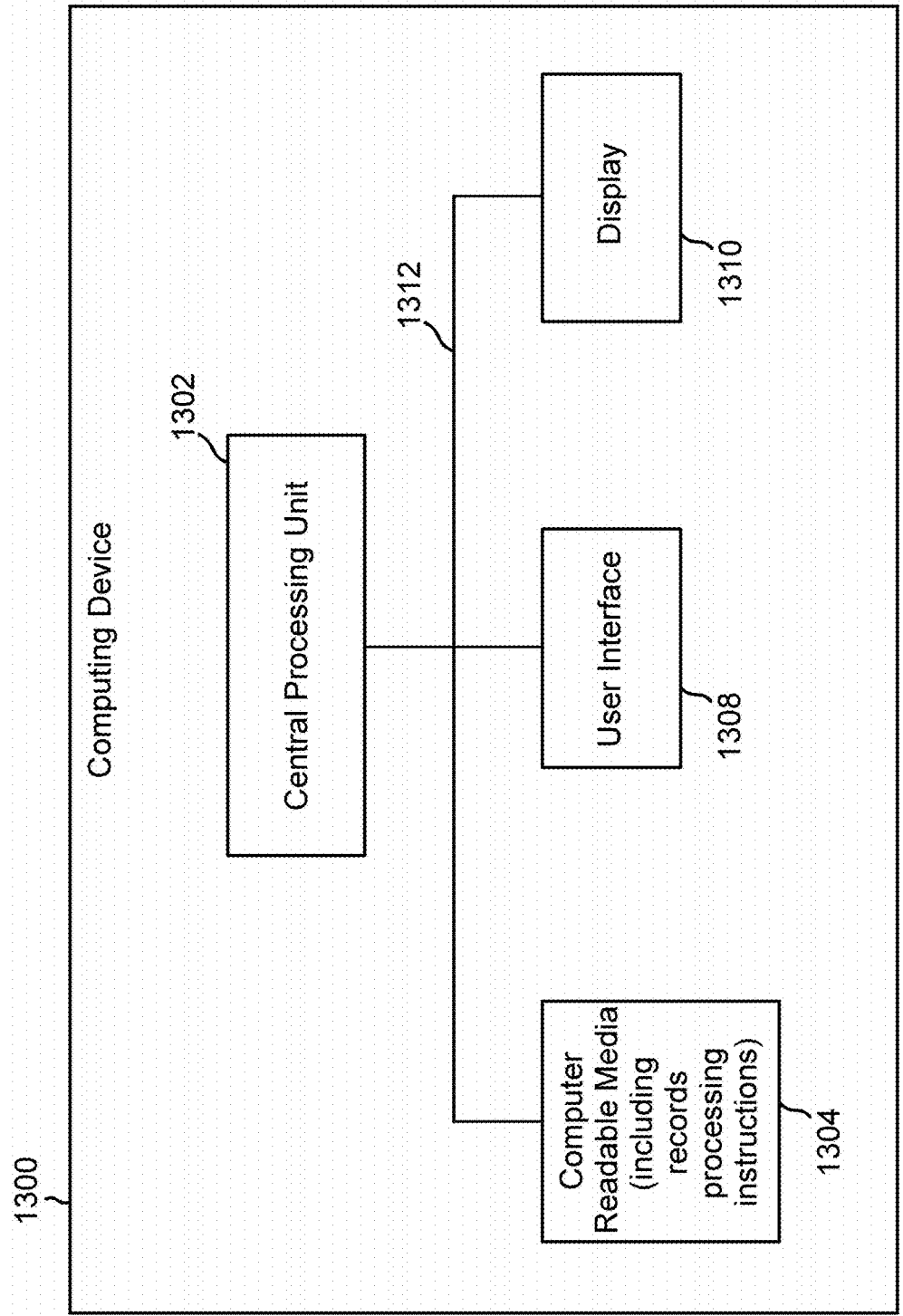
FIG. 13 is a block diagram of a computing device that includes the records processor of FIG. 2.

FIG. 13 is a block diagram of a computing device 1300 that includes the records processor 104 of FIG. 2. The computing device 1300 is specially configured to execute instructions related to the records processing described above with reference to FIGS. 3A, 3B and 3C, including the application of a deep learning algorithm to EEG records and the application of a similarities algorithm to feature vectors. The instructions are referred to below as "records processing instructions." Computers capable of being specially configured to execute such instructions may be in the form of a laptop, desktop, workstation, or other appropriate computer capable of connecting to the system 100 of FIG. 1. For example, the computing device 1300 may correspond to a programmer 116.

The computing device 1300 includes a central processing unit (CPU) 1302 that implements the various modules of the records processor 104 described above with reference to FIG. 2, and a computer readable media 1304 that includes program instructions ("records processing instructions") that enable the CPU to implement the modules of the records processor 104. The computing device 1300 also includes a user interface 1308 and a display 1310, and an interface bus 1312 that interconnects all components of the computing device.

Computer readable media 1304 suitable for storing records processing instructions include all forms of non-volatile memory, media, and memory devices, including by way of example semiconductor memory devices, flash memory devices, magnetic disks, magneto optical disks and CD ROM and DVD-ROM disks. In operation, the CPU 1302 executes the records processing instructions stored in the computer readable media 1304 to thereby perform the functions of the similarities module 202, the feature extraction module 204 and the clinical information extraction module 206 of the records processor 104 according to the methods of FIGS. 3A, 3B and 3C.

The user interface 1308, which may be a keyboard or a mouse, and the display 1310 allow for a clinician to interface with the computing device 1300 and the components of the system 100, including the database 106. For example, a clinician seeking to improve the therapy outcome of a subject patient using the system may access the database 106 through a graphical user interface (GUI) on the display 1310 and select an input record or a number of input records of a subject patient for processing. The clinician may then initiate execution of the records processing instructions stored in the computer readable media through the GUI, and await a display of the search results and relevant clinical information. The input record and search result records may be displayed as shown in FIG. 9.

Once the search results are obtained, the clinician may further interact with the system 100 through the user interface 1308 to access additional relevant clinical information stored in the database 106 associated with the search results (and the search patient associated with the search results). For example, the search patient's clinical response to a therapy (e.g., electrical stimulation) or combination of therapies (e.g., electrical stimulation and drug therapy), medical history, history of settings for an active implantable medical device (such as the values of the parameters in a neurostimulator), history of a pharmaceutical (drug) therapy (e.g., type of drug(s), dose of drug, time of delivery of dose), the outcomes or other measure of effectiveness of a given course of treatment or therapy for the search patient, and the results of an analysis of data pertaining to the search patient, such as an algorithm that classifies the search patient's EEG records into one or more types, may be accessed. The clinician may use this additional clinical information to inform her decisions regarding the neuromodulation therapies of the subject patient.

The various aspects of this disclosure are provided to enable one of ordinary skill in the art to practice the present invention. Various modifications to exemplary embodiments presented throughout this disclosure will be readily apparent to those skilled in the art, and the concepts disclosed herein may be extended to other magnetic storage devices. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A method of selecting stimulation parameter settings for a neurostimulation system associated with a patient, the method comprising:
    obtaining at least one input feature vector comprising a plurality of different features extracted by a deep learning algorithm from at least one input record of the patient;
    obtaining a set of search feature vectors, each comprising a plurality of different features extracted by a deep learning algorithm from a search record included in a set of search records of other patients;
    applying a similarities algorithm to the at least one input feature vector and the set of search feature vectors to identify a subset of search records having a measure of similarity with the at least one input record, which measure meets a predetermined criterion; and
    extracting from a database, clinical information associated with one or more of the search records of other patients in the identified subset of search records of other patients, the clinical information comprising the stimulation parameter settings of other patients for the neurostimulation system, wherein the stimulation parameter settings of other patients define a stimulation therapy deliverable by the neurostimulation system and comprise at least one of amplitude, pulse width, burst duration, and frequency.

2. The method of claim 1, wherein the extracted clinical information further comprises at least one of associated patient clinical responses, clinical history, past detection parameter settings, past stimulation settings, and past and current drug type and dosage information.

3. The method of claim 1, further comprising:
    extracting one or more search records included in the identified subset of search records from the database; and
    providing an output to a user interface, the output comprising information that enables a user device to display the one or more search records.

4. The method of claim 1, wherein obtaining at least one input feature vector comprises:
    receiving an input record of the patient; and
    applying a deep learning algorithm to the input record to extract the different features from the input record and derive a single input feature vector corresponding to the at least one input feature vector.

5. The method of claim 1, wherein obtaining at least one input feature vector comprises:
    receiving a plurality of input records of the patient; and
    separately applying a deep learning algorithm to each of the plurality of input records to extract the different features from each of the input records and derive a plurality of input feature vectors corresponding to the at least one input feature vector.

6. The method of claim 5, wherein obtaining at least one input feature vector further comprises:
applying a similarities algorithm to the plurality of input feature vectors to identify one of the plurality of input feature vectors as a single input feature vector corresponding to the at least one input feature vector.

7. The method of claim 5, wherein obtaining at least one input feature vector further comprises:
grouping the plurality of input feature vectors into sets of input feature vectors based on a common piece of information associated with the input records corresponding to the input feature vectors; and
separately applying a similarities algorithm to each set of input feature vectors to identify one of the input features vectors from each set of input feature vectors as one of the plurality of input feature vectors corresponding to the at least one input feature vector.

8. The method of claim 7, wherein the information associated with the input records indicates whether an input record resulted from one of: 1) detection of an abnormal neurological event, 2) patient initiated recording and storage, 3) periodic automated recording and storage, or 4) periodic recording and storage of baseline, normal neurological activity.

9. The method of claim 1, wherein obtaining a set of search feature vectors comprises:
receiving the set of search records of other patients; and
separately applying the deep learning algorithm to each search record in the set of search records to derive the set of search feature vectors.

10. The method of claim 1, wherein obtaining a set of search feature vectors comprises accessing a database that stores a plurality of search feature vectors.

11. The method of claim 1, wherein applying a similarities algorithm to the at least one input feature vector and the set of search feature vectors comprises, in instances where a plurality of input feature vectors is obtained, separately applying the similarities algorithm to each of the plurality of input feature vectors and the set of search feature vectors to identify a separate subset of search records for each input record.

12. The method of claim 1, wherein the input record and each search record included in the set of search records are in a same format comprising one of data sample of a time series waveform, a time-series waveform image, and a spectrogram image.

13. A processor for selecting stimulation parameter settings for a neurostimulation system associated with a patient, the processor comprising:
a similarities module configured to:
obtain at least one input feature vector comprising a plurality of different features extracted by a deep learning algorithm from at least one input record of the patient;
obtain a set of search feature vectors, each comprising a plurality of different features extracted by a deep learning algorithm from a search record included in a set of search records of other patients;
apply a similarities algorithm to the at least one input feature vector and the set of search feature vectors to identify a subset of search records having a measure of similarity with the at least one input record, which measure meets a predetermined criterion; and
an extraction module configured to extract from a database, clinical information associated with one or more of the search records of other patients in the identified subset of search records of other patients, the clinical information comprising the stimulation parameter settings of other patients for the neurostimulation system, wherein the stimulation parameter settings of other patients define a stimulation therapy deliverable by the neurostimulation system and comprise at least one of amplitude, pulse width, burst duration, and frequency.

14. The processor of claim 13, wherein the extracted clinical information further comprises associated patient clinical responses, clinical history, past detection parameter settings, past stimulation settings, and past and current drug type and dosage information.

15. The processor of claim 13, wherein the extraction module is further configured to:
extract one or more search records included in the identified subset of search records from the database; and
provide an output to a user interface, the output comprising information that enables a user device to display the one or more search records.

16. The processor of claim 13, further comprising a feature extraction module configured to:
receive an input record of the patient; and
apply a deep learning algorithm to the input record, the deep learning algorithm configured to extract the different features from the input record and derive a single input feature vector corresponding to the at least one input feature vector.

17. The processor of claim 13, further comprising a feature extraction module configured to:
receive a plurality of input records of the patient; and
separately apply a deep learning algorithm to each of the plurality of input records, the deep learning algorithm configured to extract the different features from the input record and derive a plurality of input feature vectors corresponding to the at least one input feature vector.

18. The processor of claim 17, wherein the feature extraction module is further configured to:
apply a similarities algorithm to the plurality of input feature vectors, the similarities algorithm configured to identify one of the plurality of input feature vectors as a single input feature vector corresponding to the at least one input feature vector.

19. The processor of claim 17, wherein the feature extraction module is further configured to:
group the plurality of input feature vectors into sets of input feature vectors based on a common piece of information associated with the input records corresponding to the input feature vectors; and
separately apply a similarities algorithm to each set of input feature vectors, the similarities algorithm configured to identify one of the input features vectors from each set of input feature vectors as one of the plurality of input feature vectors corresponding to the at least one input feature vector.

20. The processor of claim 13, further comprising a feature extraction module configured to:
receive the set of search records of other patients; and
separately apply the deep learning algorithm to each search record in the set of search records, the deep learning algorithm configured to derive the set of search feature vectors.

21. The processor of claim 13, wherein the clinical information further comprises detection parameter settings that define a pattern detectable by the neurostimulation system in an electrical brain activity signal sensed by the neurostimulation system, wherein a detection of the pattern by the neurostimulation system corresponds to an event.

\* \* \* \* \*